United States Patent [19]

McKinnon, Jr. et al.

[11] Patent Number: 5,505,697
[45] Date of Patent: Apr. 9, 1996

[54] ELECTRICALLY POWERED JET INJECTOR

[76] Inventors: Charles N. McKinnon, Jr., 7 Park Paseo, Laguna Niguel, Calif. 92677; James T. Potter, 6795 S.W. Larkspur Ct., Beaverton, Oreg. 97005; Ken Mattocks, 538 Hartke Loop, Oregon City, Oreg. 97045

[21] Appl. No.: 182,980

[22] Filed: Jan. 14, 1994

[51] Int. Cl.$^6$ .......................... A61M 5/30; A61M 1/00; A61M 37/00
[52] U.S. Cl. .............. 604/71; 604/152; 604/155
[58] Field of Search ...................... 604/154, 155, 604/151, 153, 131, 68, 71, 72

[56] References Cited

U.S. PATENT DOCUMENTS

| | | |
|---|---|---|
| 3,202,151 | 8/1965 | Kath . |
| 3,292,621 | 12/1966 | Banker . |
| 3,425,413 | 2/1969 | Stephens . |
| 3,507,276 | 4/1970 | Burgess . |
| 3,815,594 | 6/1974 | Doherty . |
| 3,880,138 | 4/1975 | Wootten et al. ............... 222/325 |
| 4,722,728 | 2/1988 | Dixon . |
| 4,854,324 | 8/1989 | Hirschman et al. ............. 128/655 |
| 5,066,282 | 11/1991 | Wijay et al. ..................... 604/152 |
| 5,080,648 | 1/1992 | D'Antonio . |
| 5,116,313 | 5/1992 | McGregor . |
| 5,152,776 | 10/1992 | Dinduk ........................... 606/192 |
| 5,219,099 | 6/1993 | Spence et al. ................... 222/325 |

Primary Examiner—John D. Yasko
Assistant Examiner—Adam J. Cermak
Attorney, Agent, or Firm—Lyon & Lyon

[57] ABSTRACT

An electrically powered jet injector impacts a plunger driver against a plunger to generate a high initial pressure pulse, for piercing the skin. The plunger driver then continues to generate a lower delivery pressure until the injection is completed. A microprocessor within the injector controls the speed and direction of the electric motor which moves the plunger driver. The injector provides a subcutaneous injection especially useful for injecting insulin to treat diabetes.

22 Claims, 23 Drawing Sheets

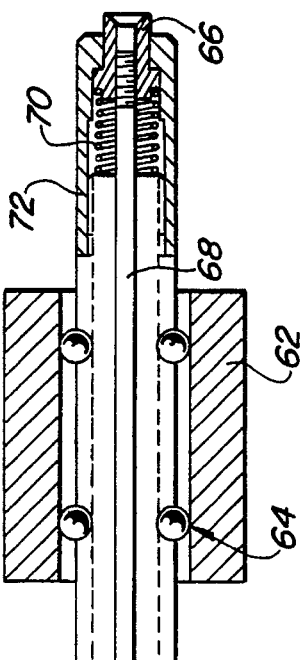
Fig. 5
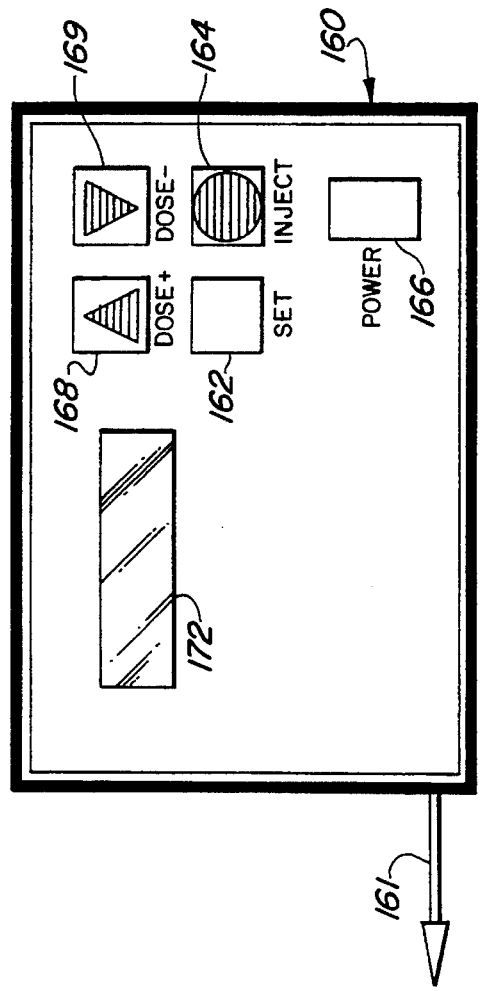
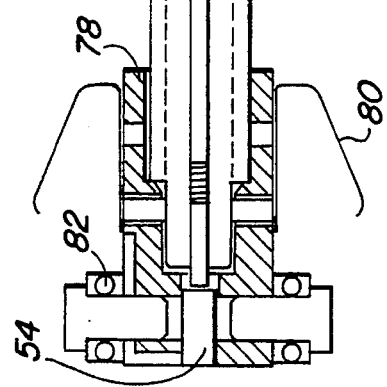
Fig. 6

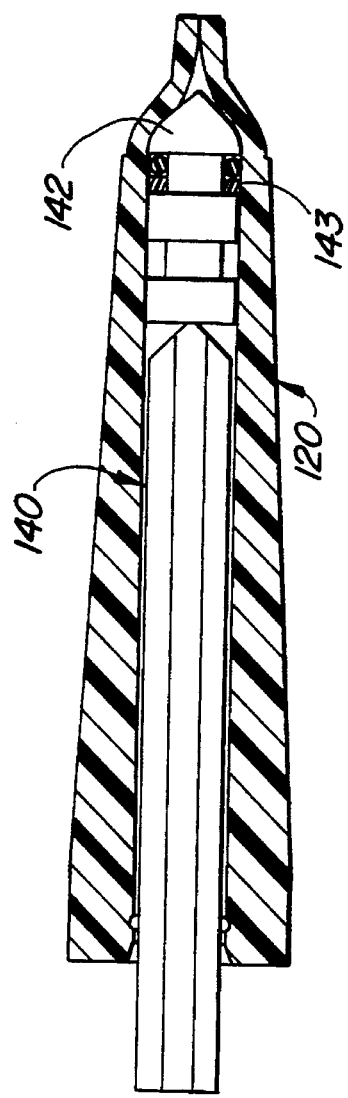
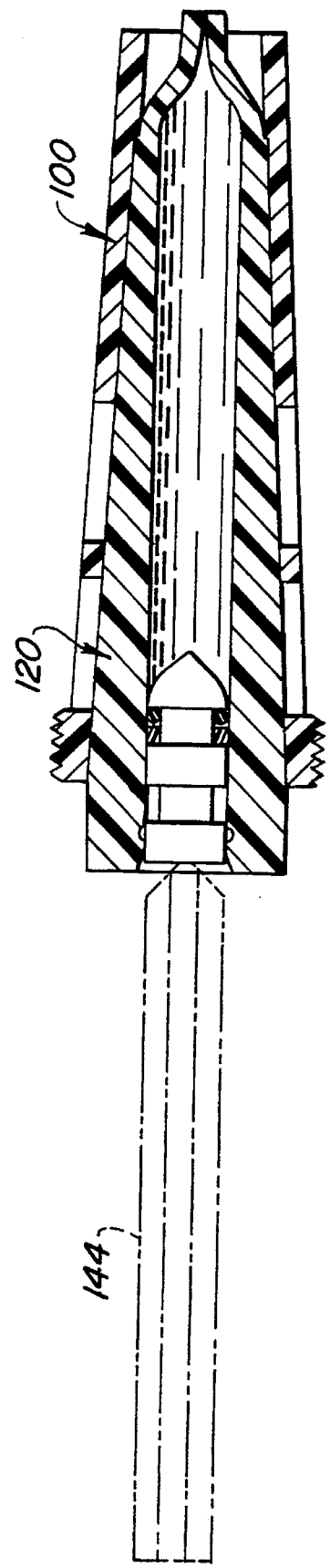

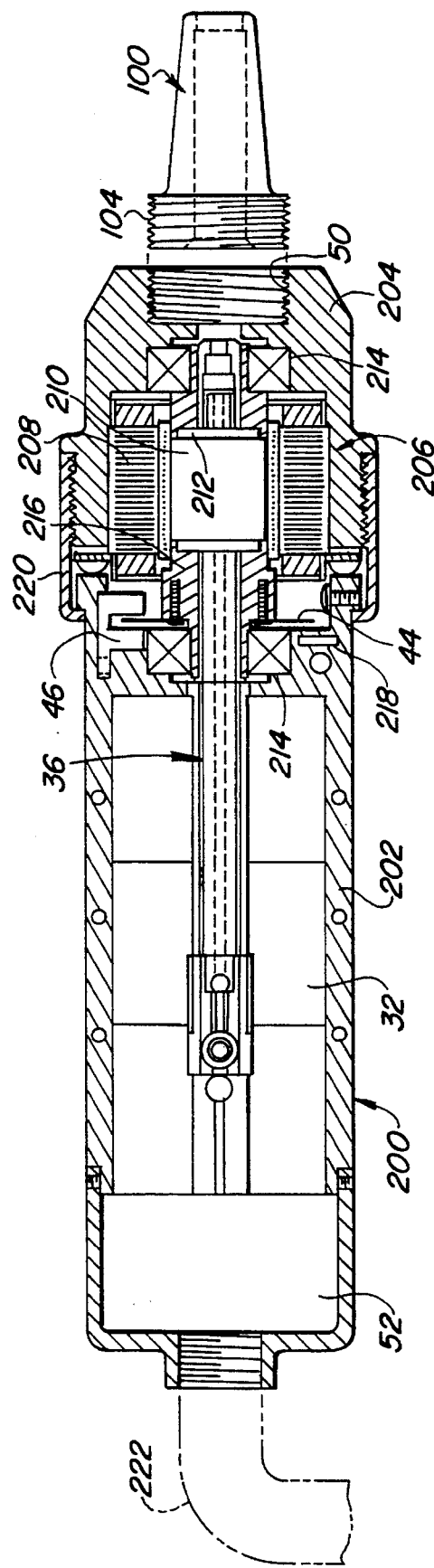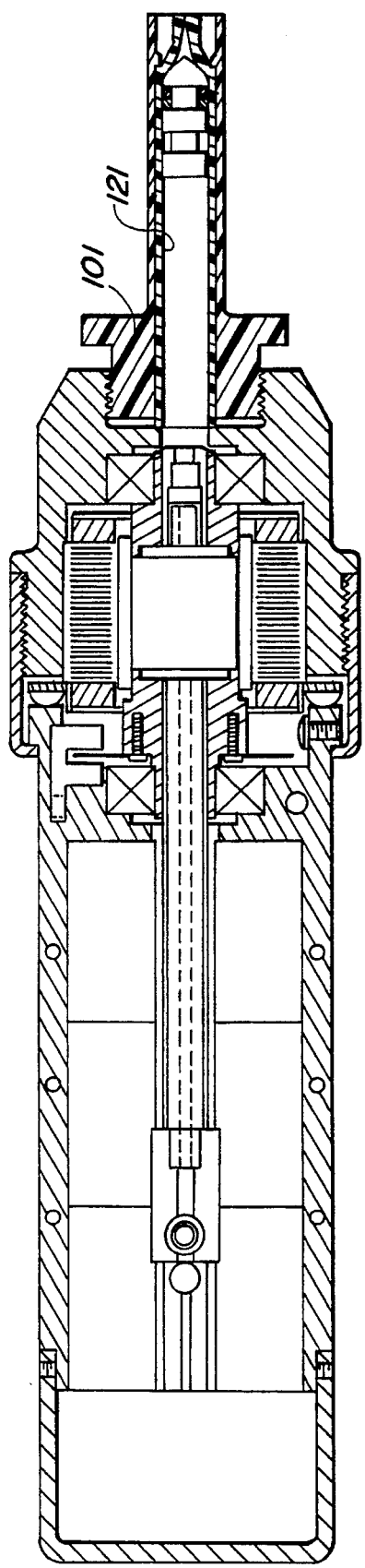
Fig. 14A
Fig. 14B

ELECTRICALLY POWERED JET INJECTOR

BACKGROUND OF THE INVENTION

The field of the invention is jet injection methods and devices.

Various jet injection methods and devices have been known and used in the past. Jet injection devices typically have primarily used compressed gas or springs to rapidly drive a piston or plunger into an ampule having a small diameter nozzle. The high fluid pressure within the ampule, generated by the large force on the plunger, causes a jet or stream of fluid to flow from the nozzle at a pressure and velocity sufficient to penetrate the skin.

Jet injection has several advantages over conventional needle and syringe injections. The patient may be more relaxed as no needle is used. Pain experienced during the injection may also be lessened in certain instances. More importantly, after the injection, there is no risk of an accidental stick or puncture with the used needle, thereby significantly reducing the risk to doctors, nurses and others of transmission of infectious disease. In addition, special handling and disposal requirements for the potentially hazardous used needle are lessened.

One area where jet injection would be very helpful is in the treatment of diabetes. Patients with chronic diabetes generally must inject themselves with insulin several times during the day. This procedure requires a continuous supply and repeated handling of needle/syringe combinations, syringe filling steps, and safe and sterile storage of the needle/syringe in between injections. However, insulin injected with a needle/syringe has a certain well known advantageous time-action profile, i.e., the formulation of the insulin, the characteristics of the injection site, and the way the insulin is delivered by the needle into the injection site, combine to allow the insulin to be absorbed into the patient's blood at the desired rate.

As shown in FIG. 1, using a needle/syringe 1, insulin 2 is delivered through the skin 3 into the adipose tissue 4. The adipose tissue is made up of fat and connective tissue. The injected volume of insulin typically forms a bolus 5 in the adipose tissue. The needle/syringe uses low pressures. Consequently, the injected fluid seeks a path of least resistance, approximately isotropic in the adipose tissue. As a result, the injected fluid forms into a bolus generally having a ragged or irregular generally spherical or globular shape. This shape of insulin volume causes a slow absorption of the insulin into the blood. Moreover, blood circulation in the adipose tissue surrounding the bolus is generally relatively low, further slowing the absorption of insulin into the blood. Consequently, the needle/syringe delivery achieves a desired time-action profile of insulin level in the blood.

The use of jet injection for administration of Insulin dates back to at least as early as 1966. In that era, the standard Insulin was fairly quick acting, so patients received several small injections over the course of a day. It has long been recognized that keeping the Insulin level more nearly constant in the bloodstream of diabetics would improve their long term survival, and mitigate some of the complications that result from deviations in Insulin level from the desired natural level. Thus, longer acting formulations of Insulin were sought, and became available to patients in the 1980's. However, these longer acting Insulins were formulated to get the proper time-action profile with a needle/syringe. When these same formulations were administered with previous jet injectors, results were not satisfactory. Jet injection of these Insulins, have produced much faster absorption of the Insulin than desired.

This disadvantage of jet injection arises because jet injection necessarily uses high pressures to create a high velocity fluid jet. As shown in FIG. 2, after piercing the skin, the jet 6 forms a deposit 7 in the adipose tissue which is elongated and directed toward the muscle fascia 8. The much higher blood circulation in the muscle 9 and the muscle fascia 8 boundary produce much faster absorption of the insulin (or other injectant) into the blood stream. In addition, the high velocity of the injected jet causes mixing of the fluid with the adipose tissue, again promoting a more rapid than desirable absorption into the blood stream. Thus, jet injection, despite its advantages, has not been generally acceptable for diabetics using modern long acting Insulin formulations.

SUMMARY OF THE INVENTION

The present invention is directed to an improved jet injection method and device. To this end, a jet injector includes a plunger driver which impacts against a plunger to generate a high initial pressure pulse, for piercing the skin. The plunger driver then continues to generate a lower delivery phase pressure until the injection is virtually completed. The invention is especially useful for injecting insulin to treat diabetes.

Accordingly, it is an object of the invention to provide an improved jet injection method and device.

BRIEF DESCRIPTION OF THE DRAWINGS

Other objects and features of the present invention will become apparent from the following detailed description taken in connection with the accompanying drawings which disclose embodiments of the invention. It is to be understood, however, that the drawings are designed for the purpose of illustration only and are not intended as a definition of the limits of the invention.

In the drawing, wherein similar reference characters denote similar elements throughout the several views:

FIG. 5 is a plan view of a control panel for the device of FIG. 3;

FIG. 6 is a side elevation view in part section of the ball screw and nut shown in FIG. 3;

FIG. 12 is a side elevation view in part section of the assembled sleeve, ampule, and plunger of FIGS. 8, 9, and 10, with the plunger fully advanced and ready for filling the ampule;

FIG. 13 is a similar side elevation view in part section showing the plunger fully retracted and the ampule filled with injectant;

FIG. 14A is a section view of an alternative embodiment injector; and

FIG. 14B is a section view thereof with the ampule and sleeve of FIGS. 8B and 9B attached;

DESCRIPTION OF THE PREFERRED EMBODIMENT

Figure 1:
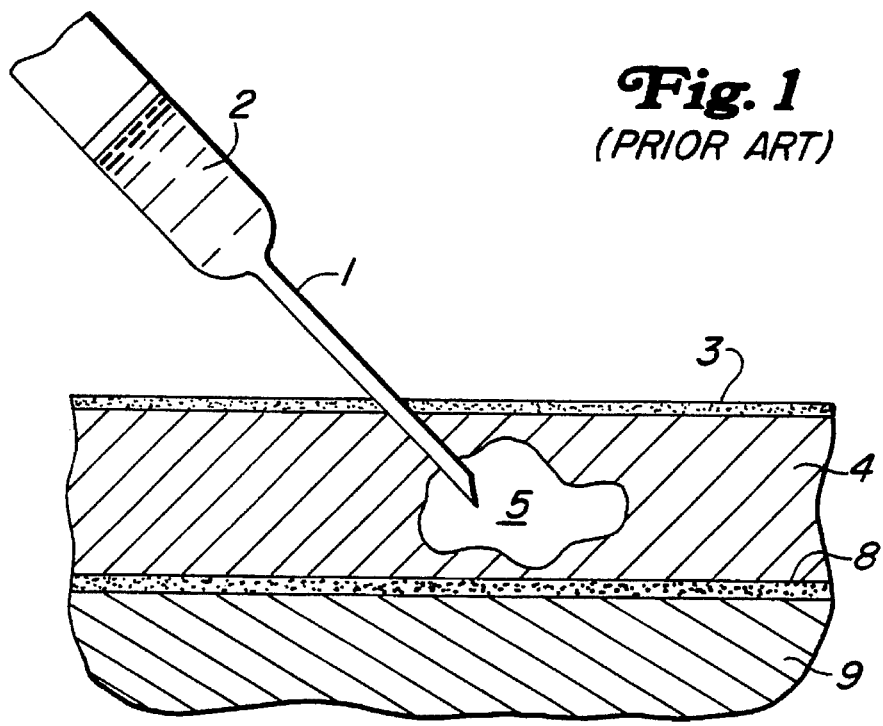
FIG. 1 is a schematic illustration of a needle/syringe injection.
Figure 2:
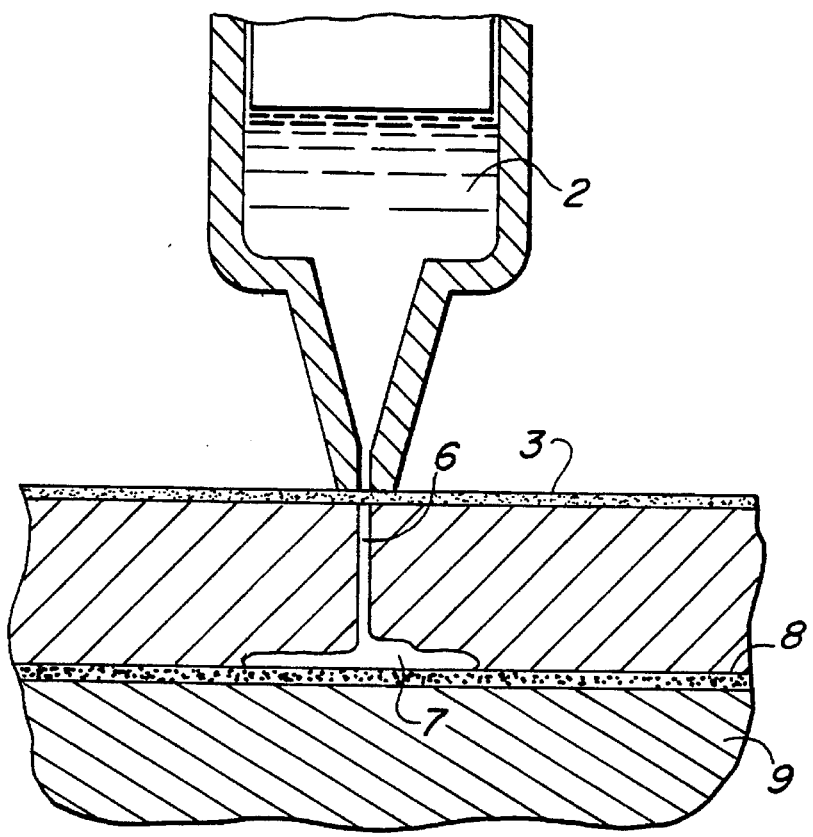
FIG. 2 is a schematic illustration of a jet injection.
Figure 4:
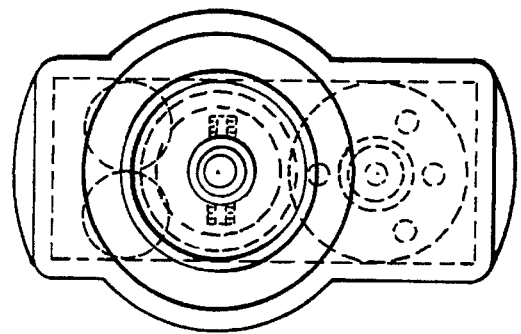
FIG. 4 is an end view thereof.
Figure 3:
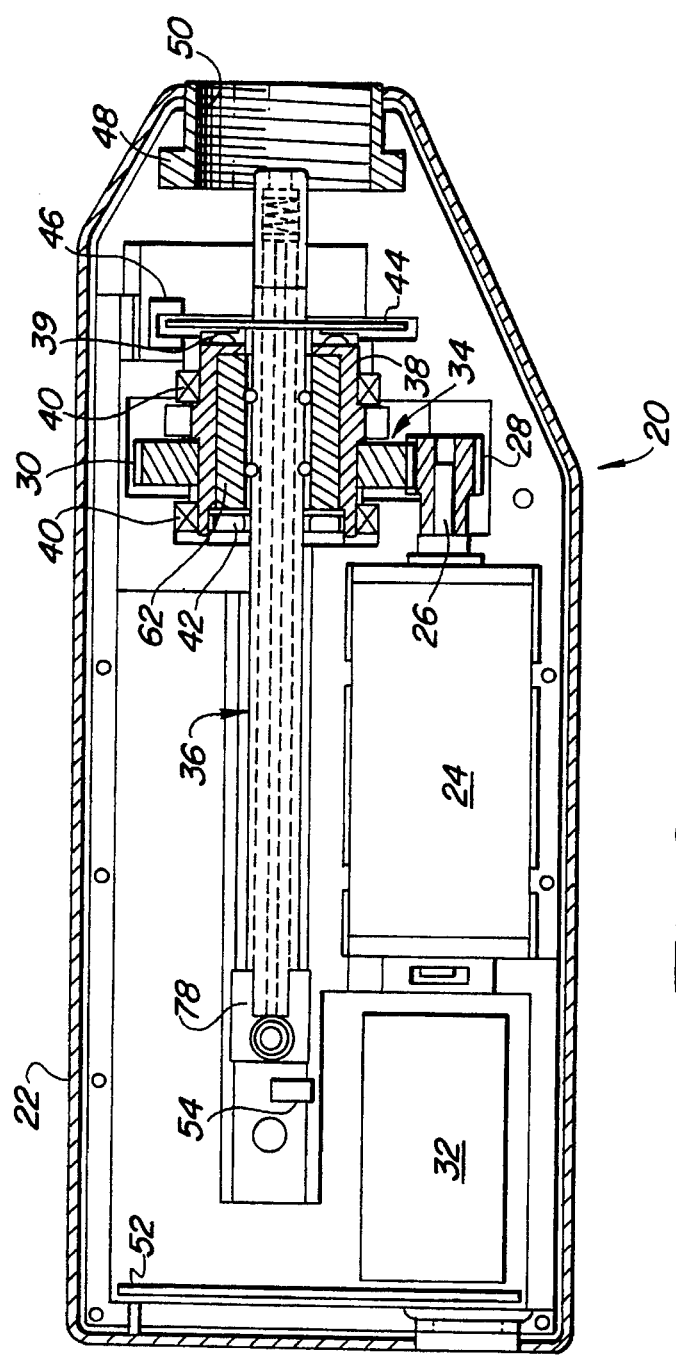
FIG. 3 is a section view of the present injection device.

As shown in FIG. 3, a first preferred embodiment of the injector 20 includes a housing 22 containing an electric motor 24 powered by batteries 32. The motor 24 in the embodiment of FIG. 3 is a DC moving coil motor, for fast response. A pinion 28 is attached to the motor shaft 26 and meshes with spur gear 30 attached around a nut sleeve 38. A wave washer 39 biases the nut sleeve 38 towards the rear of the housing 22 to help reduce the mechanical compliance of the system and contribute to a faster injection pressure rise time.

The nut sleeve 38 surrounds a ball screw assembly 36 and is radially supported by a pair of spaced apart radial bearings 40, and is axially supported by a thrust bearing 42. An encoder wheel 44 is attached to the front end of the nut sleeve 38. An encoder pick up 46 attached to the housing 22 is positioned around the outside perimeter of the encoder wheel 44. A threaded insert 48 is positioned at the front end of the housing 22 and has internal threads 50. A detection switch 54 adjacent the back end of the ball screw assembly 36 is electrically linked to the power switching circuit board 52. The detection switch is mounted on an end fitting 78 attached to the ball screw and it moves longitudinally with the ball screw.

Turning to FIG. 6, the ball screw assembly 36 includes a ball nut 62 having a recirculating ball circuit 64 positioned around a ball screw 60. A switch actuator cap 66 is secured within an end cap 72 at the forward end of the ball screw assembly 36. A spring 70 biases the switch actuator cap 66 forwardly. A switch rod 68 is threaded into the switch actuator 66 and extends entirely through a bore in the ball screw 60.

The end fitting 78 contains trunion bearings 82 which fit in slots in body housing 22, and prevent the ball screw 60 from rotating, while allowing it to longitudinally advance and retract. Contact or slip springs 80 on the end fitting 78 slide along channels in the body housing 22 and electrically link the detection switch 54 to controller board 190. The detection switch 54 is actuated by longitudinal movement of the switch rod 68.

Figure 8A:
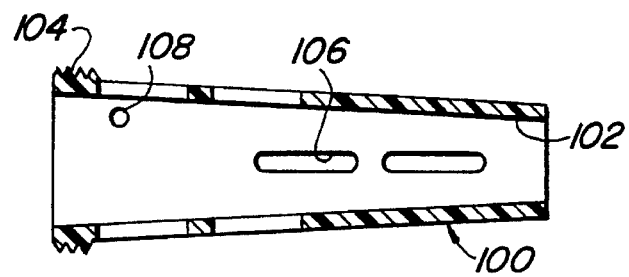
FIG. 8A is a section view of a tapered wall ampule sleeve.
Figure 8B:
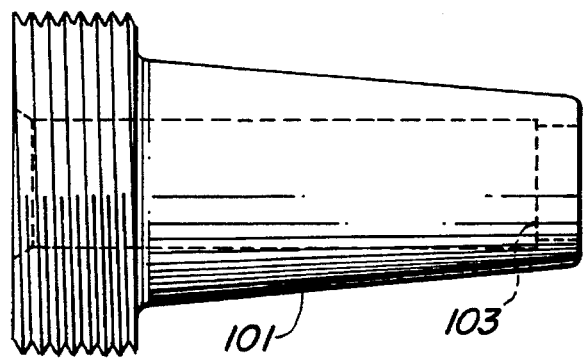
FIG. 8B is a section view of a straight wall ampule sleeve.

As shown in FIG. 8A, an ampule sleeve 100 has a tapered inner surface and a threaded back end 104, for threading into the internal threads 50 on the threaded insert 48 of the injector shown in FIG. 3. Viewing slots 106 extend through the tapered tubular body of the ampule sleeve 100. A spanner fitting or hole 108 is provided on the ampule sleeve, so that it may readily be tightened into the threaded insert 48. A similar ampule sleeve 101, as shown in FIG. 8B, has straight inner walls and a stop 103.

Figure 9A:
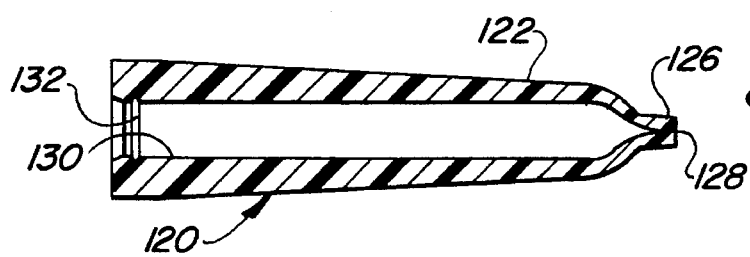
FIG. 9A is a section view of a tapered wall ampule used with the sleeve of FIG. 8A.
Figure 9B:
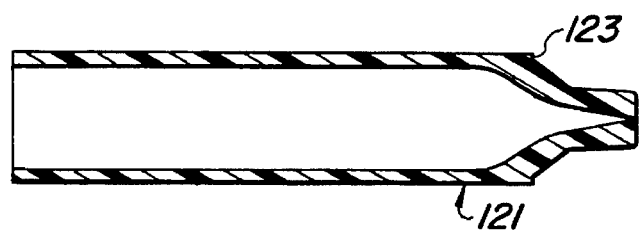
FIG. 9B is a section view of a straight wall ampule used with the sleeve of FIG. 8B.

Referring to FIG. 9A, an ampule 120, preferably molded of plastic, has a tapered outer surface 122. A luer fitting 126 surrounds the nozzle 128 of the ampule 120. The nozzle 128 preferably has a diameter of about 0.003–0.004 inches. A cylindrical injectant chamber 130 is formed within the ampule, and an annular recess 132 is located at the back end of the injectant chamber 130. An alternative ampule 121, as shown in FIG. 9B has straight walls thinner than the ampule 120.

Figure 10:
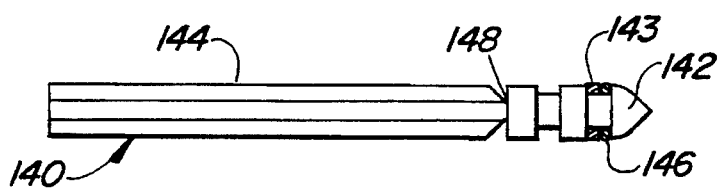
FIG. 10 is a side elevation view of a plunger.

With reference to FIG. 10, a plunger 140 includes a plunger head 142 attached to an extension 144 through a frangible joint 148. An o-ring 146 is positioned in a slot on the plunger head 142 along with a Teflon backup ring 143. Turning to FIG. 13, the tapered outer surface 122 of the ampule 120 is dimensioned to match with the tapered inner surface 102 of the ampule sleeve 100, generally forming a line to line fit of the ampule 120 within the ampule sleeve 100. The preferably metal sleeve supports the ampule walls against the fluid pressure exerted on them during injection. The plunger 140 is slidably engaged through the injectant chamber 130 of the ampule 120.

Referring again to FIGS. 8B and 9B, in alternate embodiment, the ampule 121 having straight walls is positioned inside of the sleeve 101, with the ampule shoulder 123 against the stop 103. The sleeve I.D. is preferably 0.002 inch maximum larger in diameter than the O.D. of the ampule 121. The thin walls of the ampule 121 do not alone significantly resist injection pressures. Rather, they expand radially during injection, until they contact the I.D. of the sleeve, at which time the steel sleeve contributes the majority of the mechanical system stiffness.

FIG. 5 shows a control panel provided on the outside of the injector 20. Alternatively, the control panel may be included on a separate control box electrically linked to the injector 20 via a cable 161 and housing connector 180. The control panel 160 includes the display 172, a power rocker switch 166, increase and decrease dosage switches 168 and 169, a dosage set switch 162 and an inject switch 164.

Figure 7A:
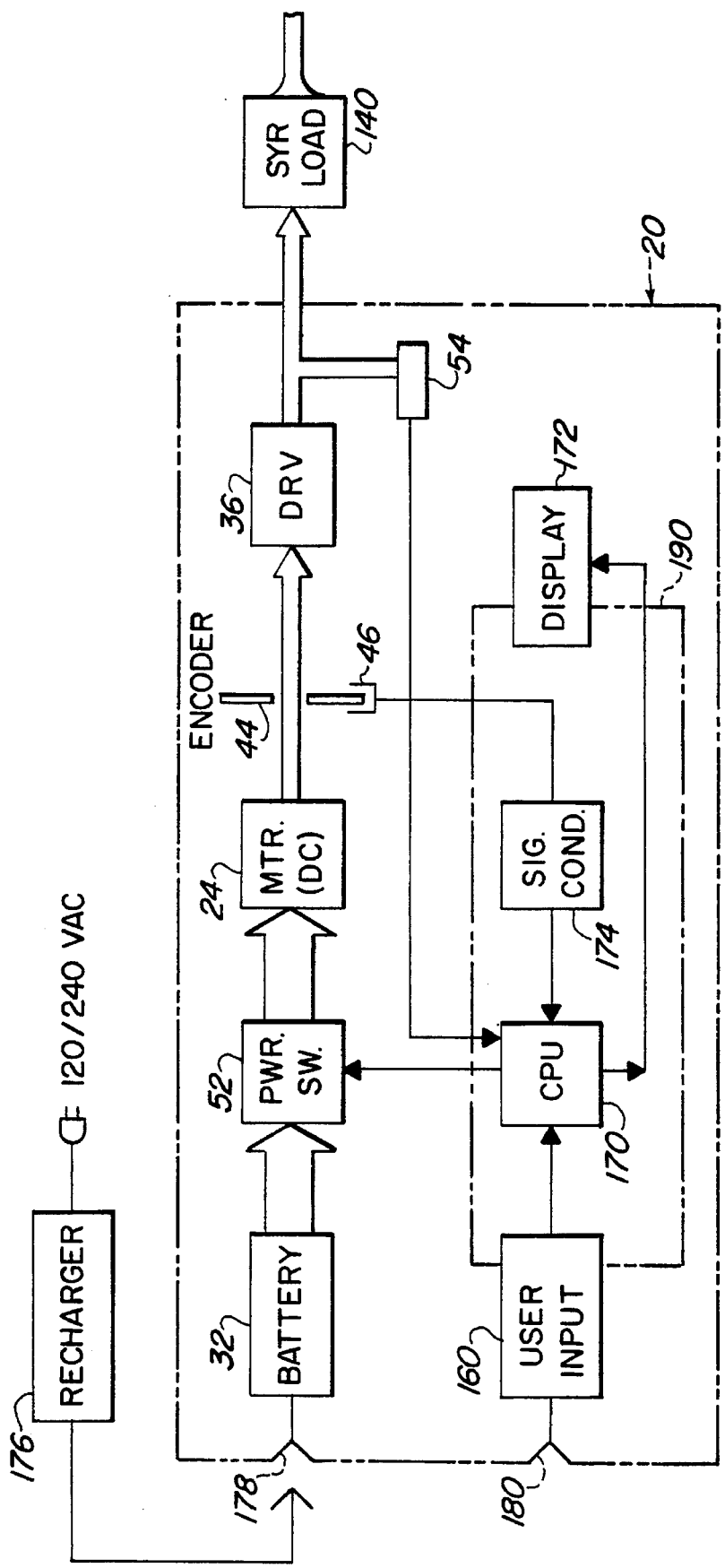
FIGS. 7A and 7B are schematic block diagrams of the injector of FIG. 3.
Figure 7B:
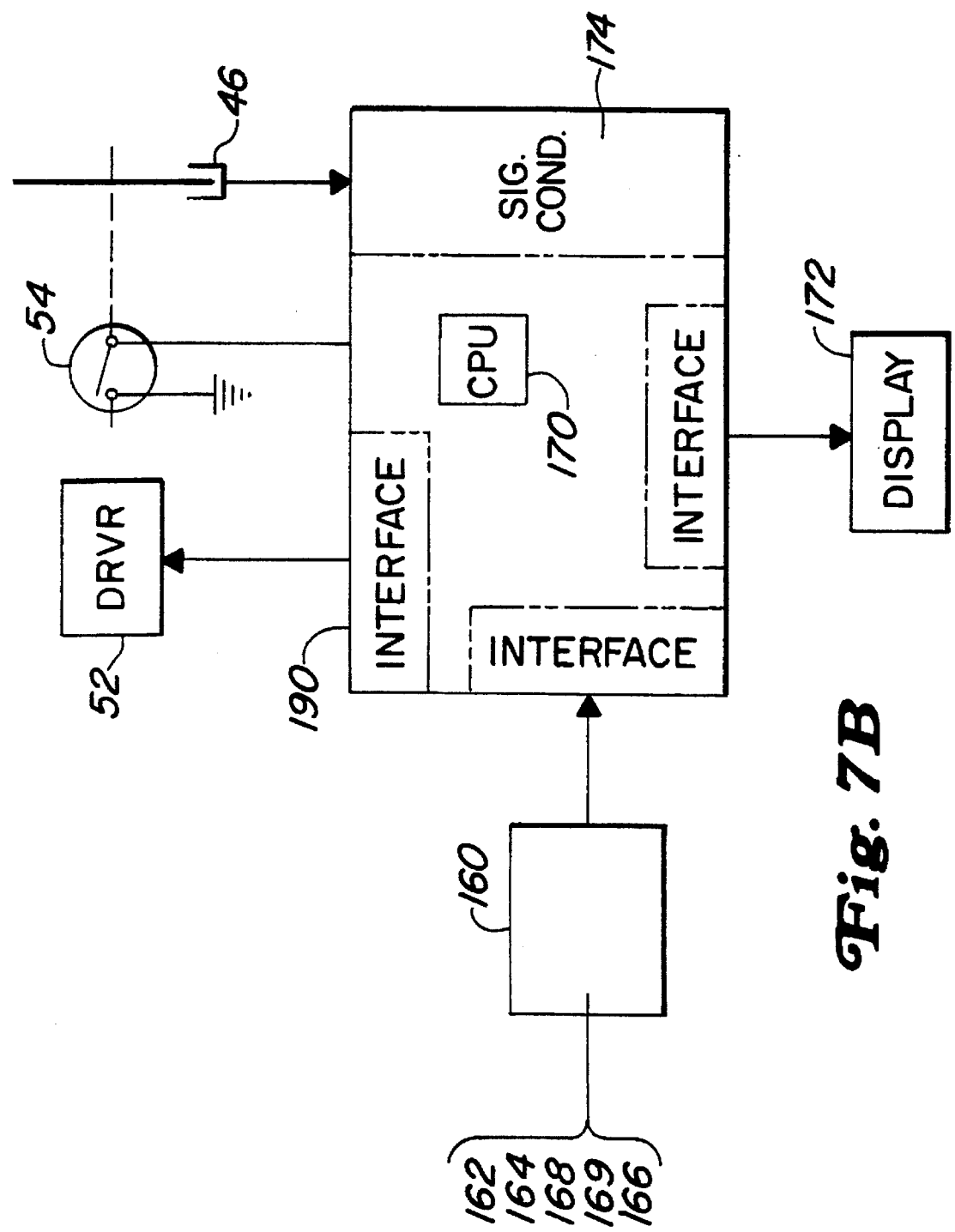

FIGS. 7A and 7B schematically illustrate the injector 20 shown in FIG. 3. A central processing unit (CPU) 170 on the controller board 190 is linked to a display 172 on the control panel 160. The CPU 170 is also linked to the user input switches on the control panel 160, to signal conditioning circuitry 174, for conditioning signals from the encoder pickup 46, and to the detector switch 54. The power switching circuit board 52 is the primary output from the CPU 170. Its functions include switching of battery voltage to the motor 206, either as a steady voltage, or under pulse width modulated conditions (PWM), as determined by the CPU 170.

The encoder wheel 44 and pick up 46, in connection with the CPU 170, incrementally count pulses resulting from the encoder wheel 44 spinning with the ball nut. The signal conditioning circuitry 174, also located on the circuit board 52 provides a velocity and volume indication to the CPU 170. The display 172 is driven by interface components and the CPU 170. A battery recharger 176 may also be linked to the batteries 32 via a cable and connector 178 on the injector housing 22.

FIGS. 14A and 14B shown shows a second preferred embodiment injector 200 having a front housing 204 and a tubular rear housing 202. The front housing 204 contains a hollow core motor 206 having a stator 208 attached to the front housing 204. The rotor 210 of the hollow core motor 206 is bonded onto a ball nut 212 of a ball screw assembly 36. A ball nut sleeve 216 joined to the ball nut 212 extends longitudinally to retain ball bearings 214 in front and in back of the motor 206. An optical encoder wheel 44 is attached to the back surface of the nut sleeve 216. As the encoder wheel 44 spins, it interrupts an infra-red light beam emitted by the encoder pick up 46. A Hall switch plate assembly 218 positioned behind the motor 206 electronically commutates the electrical current to the motor. The motor 206 is brushless and has no commutator or brushes to wear out. Drive circuitry is located on the power switching board 52 at the back end of the device 200.

In addition to being more compact than the embodiment of FIG. 3, the embodiment 200 shown in FIG. 14A eliminates the use of gears to reduce the drive speed of the motor to a lower speed appropriate for driving the ball nut. The absence of gears in the injector 200 is compensated for by using a finer pitch on the ball screw assembly 36. Alternatively, a hollow planetary gear design may be used with the hollow core motor 206. The injector 200 preferably also has closed loop motor control, whereas the injector 20 does not.

Referring still to FIG. 14A, the batteries 32 are clustered around the ball screw assembly 36 towards the back end of the injector 200, with the power switching board 52 positioned behind the batteries. A union nut 220 holds the front housing 204 onto the rear housing 202. The design principles of the ball screw assembly 36 and components for actuating the detection switch 54 are similar to those described above in connection with the embodiment of FIG. 3, although the ball screw may be provided with a finer pitch. If the controls are contained in a separate unit, a cable and connector 222 may be provided at the back end of the injector 200 to link the injector and control unit.

Figure 11:
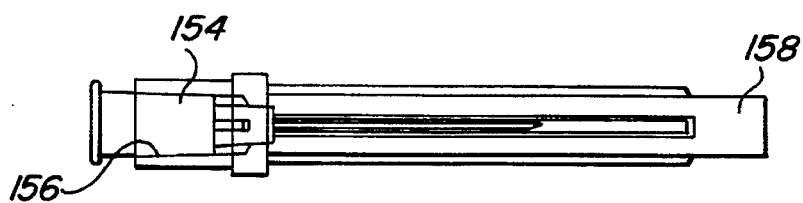
FIG. 11 is a side elevation view of a filling needle for use with the ampule of FIG. 9.

In use, the ampule 120 or 121 and plunger 140 are provided in a sterile "peel-pack", along with a filling needle 154 covered by a protective cap 158, as shown in FIG. 11. The plunger 140 is fully advanced into the ampule, as shown in FIG. 12. The peel-pack is opened and the filling needle 154 attached to the front end of the ampule via the luer fitting 126 and 156 on the ampule and on the filling needle 154. The protective cap 158 is removed. The filling needle 154 is inserted into a vial containing the liquid injectant. The plunger extension 144 is withdrawn until the frangible joint 148 is located just outside of the end of the ampule. The extension 144 is then moved from side to side until it breaks off, leaving only the plunger head 142 remaining inside the ampule. The preferred maximum volume contained within the ampule 120 or 121 is approximately 2.5 ml. The filling needle 154 is removed from the ampule and is discarded. The filled ampule is then placed within the ampule sleeve 100 or 101, as shown in FIG. 13. The slots 106 in the ampule sleeve allow visual inspection of the fluid contents of the ampule. In ordinary use, it can be expected that the approximately 2.5 ml volume of liquid injectant will last approximately 3 days, when dispensing doses of insulin to a typical diabetes patient.

The ampule sleeve is threaded into the internal threads 50 on the front housing 204 of the injector 200. A spanner wrench, engaging the hole 108 (FIG. 8) in the ampule sleeve 100 may be used to tighten the sleeve into the front housing 204.

The power switch is turned on. The controller (or CPU 170) immediately actuates the first phase of the injection operation which is the "find volume" phase. The primary purpose of this phase is to locate the end of the plunger head 142 and establish a run-up gap. The injector 200 performs this step by driving the motor slowly in reverse until the ball screw engages a hard stop, i.e., the end fitting 78 contacts a stop on the inside of the housing. The CPU records the stop position, i.e., the turns count of the encoder is set to zero. Then, the battery condition may optionally be tested by switching the motor on fast for a short time and measuring turns of the ball nut. Next, the motor is switched on to slowly advance the ball screw under PWM until switch actuator cap 66 at the front of the ball screw touches the plunger head 142 and actuates the detection switch 54. With the ball screw resting against the back of the plunger head 142, the CPU determines and displays the "volume left" in ampule, based on the numbers of screw turns counted by the encoder, which is proportional to distance traveled by the ball screw and the volume of injectant in the ampule. If the volume left is too little or if no plunger head is detected, warnings may be displayed.

Using the injector 20, the next step in the method is to back off the ball screw to set the gap. The microprocessor determines how much of a gap is required, using a look up table. The gap is made long enough to allow the motor 206 (and correspondingly the ball screw) to accelerate up to the desired impact speed. The look up table may factor in battery condition, changes in the mechanical system compliance, etc. The injector 200, having closed loop control wherein motor speed is controlled at impact sets a gap which may be a fixed dimension, e.g., ¾ inch.

Next, the desired dose is set by using the dose increase/decrease buttons 168 and 169 shown in FIG. 5. Changes in the dose are shown on the display 172. By pushing the set button 162, the dose selected is recorded or locked into memory within the CPU 170. The display 172 then indicates e.g., "vol. set at 30 units". With the injector 200 now ready to inject, the nozzle end of the ampule 120 is placed against the skin at the injection site.

To initiate the actual injection, the patient then pushes the inject button 164. The CPU 170 activates electronic switches on the power switching circuit board 52 to start the motor. The rotation of the rotor causes the ball nut to turn. The ball nut interacts with the ball circuit 64 to longitudinally advance the ball screw 60 toward the rear face of the plunger head 142. The motor 26 in the embodiment of FIG. 3, accelerates and causes the ball screw to impact the plunger head at a velocity determined primarily by the gap. The motor, 206 in the embodiment of FIG. 14 reaches a peak, controlled speed before the ball screw 60 impacts on the plunger head 142. An impact speed of about 4 in./sec. is typical. Upon impact, the switch rod 68 contacts the plunger head 142 and moves rearwardly with respect to the advancing ball screw 60, compressing the spring 70 and actuating the detection switch 54. Thus, the gap set in the device of FIG. 14 allows the motor 206 sufficient time for acceleration, but does not control impact speed, as in the injector of FIG. 3.

When the detection switch 54 is actuated, the counter register in the CPU 170 is reset. The encoder wheel 44 then provides pulses indicative of the volume of fluid delivered, as the plunger head 142 and ball screw 60 move forward.

The impact of the ball screw 60 at a pre-determined velocity into the plunger head 142 provides a very fast rise in ampule pressure. At impact, the rotary energy decreases as pressure energy builds up in the ampule, at a rate controlled by the compliance of the ampule sleeve assembly. The peak pressure reached is determined primarily by the initial impact velocity, and the system compliance.

Figure 15:
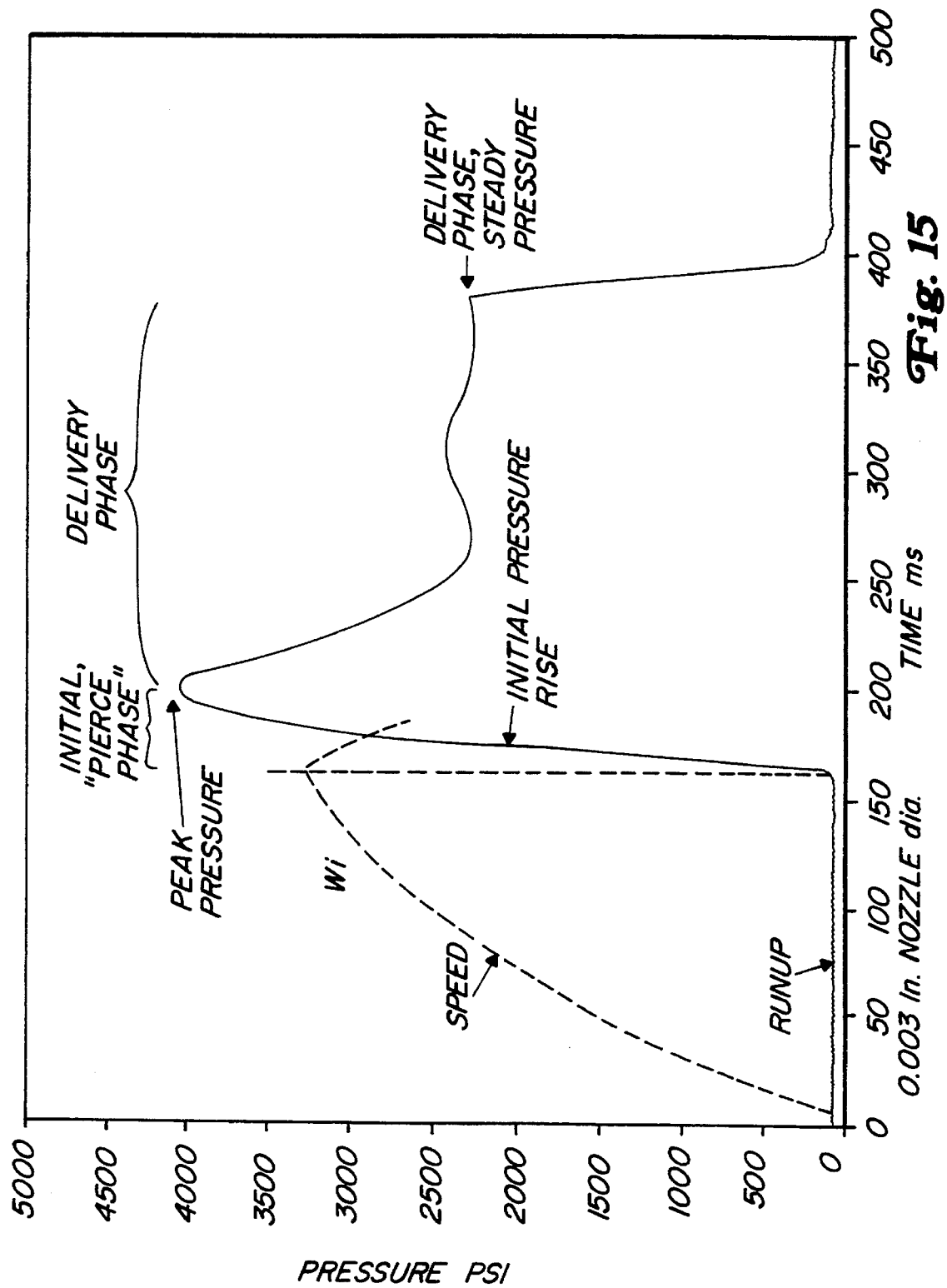
FIG. 15 is a graph of actual pressure versus time of a test injection provided by the injector shown in FIG. 3, using a 0.003 inch nozzle diameter.

Referring to FIG. 15, during the initial pierce phase of the injection, there is a very fast pressure rise to a peak pressure of about 4,000 psi. This peak pressure serves to pierce the skin and generate a short, slightly elongated channel in the sub-cutaneous tissue. The ampule nozzle diameter is about 0.003–0.004 inches. At about the time the initial pressure peak is reached, the CPU 170 provides new commands to the power switching circuit board 52, to provide a motor speed which delivers steady state delivery pressure. The CPU 170 determines when impact occurs by storing the count elapsed from the previously set gap and location of the plunger head 142, determined in the set up phase. Thus, at a pre-determined count after the ball screw begins to traverse the gap, the CPU reduces the motor speed for the delivery phase.

The delivery pressure is typically between about ½ and ⅓ of the peak pressure achieved. The lower delivery pressure minimizes the (fluid momentum x time) directed toward the muscle. This helps by containing all of the injected fluid in a volume or bolus having a minimal surface area, all within the subcutaneous tissue. High pressures are necessary only for a very short duration, to pierce the skin and make a nominal channel into the underlying tissue. Then, the following low, steady delivery pressure only fills the existing channel with fluid, without further tissue disruption.

Control of pressure in the delivery phase is provided by closed loop regulation of the motor speed. Specifically, pulse width modulation (PWM) is used, wherein the "on-time" of a fixed frequency pulse generator in the CPU 170 is varied to modulate the average current provided to the motor 206. The closed loop control allows the device 200 to compensate for variations in battery voltage, friction due to wear or environment temperature changes, or variations in ampule parameters, especially plunger friction.

The encoder is used as a counter of either motor or ball screw revolutions, which are proportional to volume change in the ampule. When the ball screw 60 and the plunger head 142 move forward to the location wherein the accumulated pulses detected from the encoder wheel 44 equals the number set during the set up phase as the "desired volume", the CPU 170 cuts off current to the motor 206. Alternatively, applying "crow bar" (short circuit), or reverse current to the motor 206 may be used to provide a sharp cut off for enhanced dose precision. The display indicates the actual dose delivered. The CPU 170 then enters a reset phase wherein the ball screw 60 is retracted.

Preferably, after the injection, the ampule is pressed against the injection site for 5 seconds to ensure that all transient pressures inside the tissue are equalized. This duration minimizes fluid weep-back when the injector is removed from the injection site.

Thus, as shown, a primary principle of operation of the injector 200 is control of pressure in the ampule 120 by properly measuring and regulating the speed of the motor 206. FIGS. 17–30 show flow charts for controlling the injector. Corresponding microprocessor code is included in the Appendix.

Figure 16:
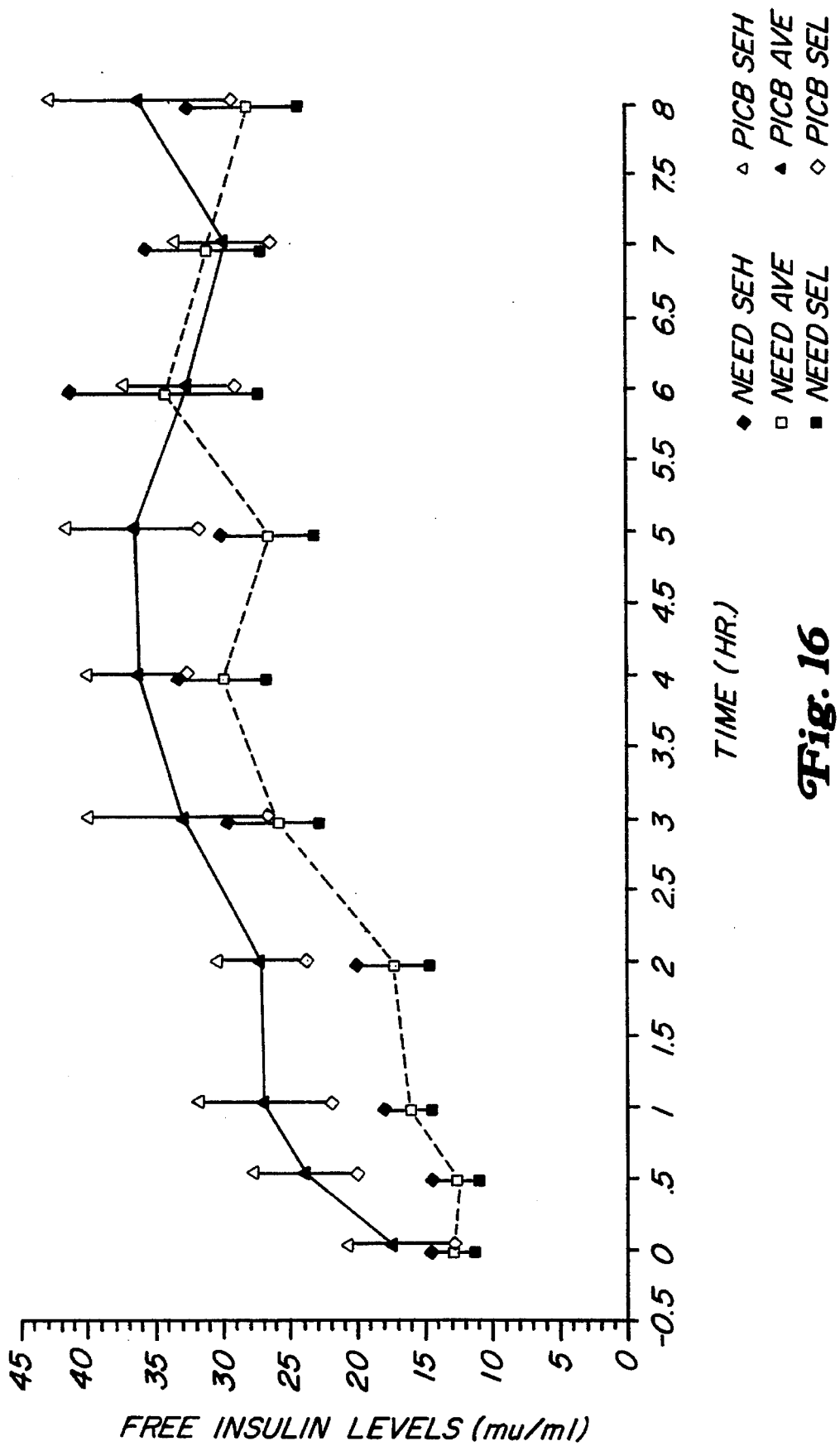
FIG. 16 is a graph of Insulin absorption over time comparing the present injector and method to a needle/syringe.
Figure 17:
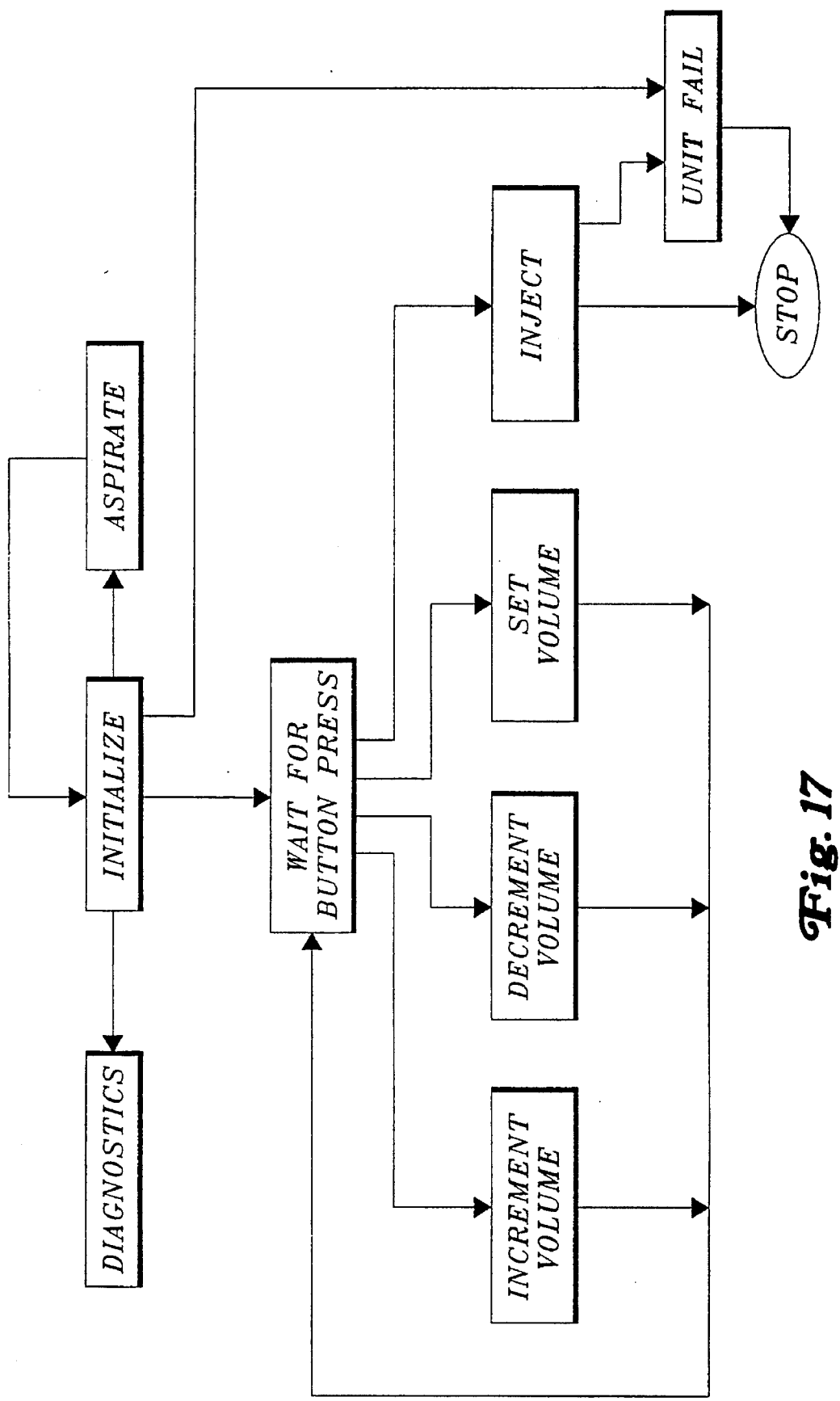
FIGS. 17–31 are flow charts showing operation of the present injector.
Figure 18A:
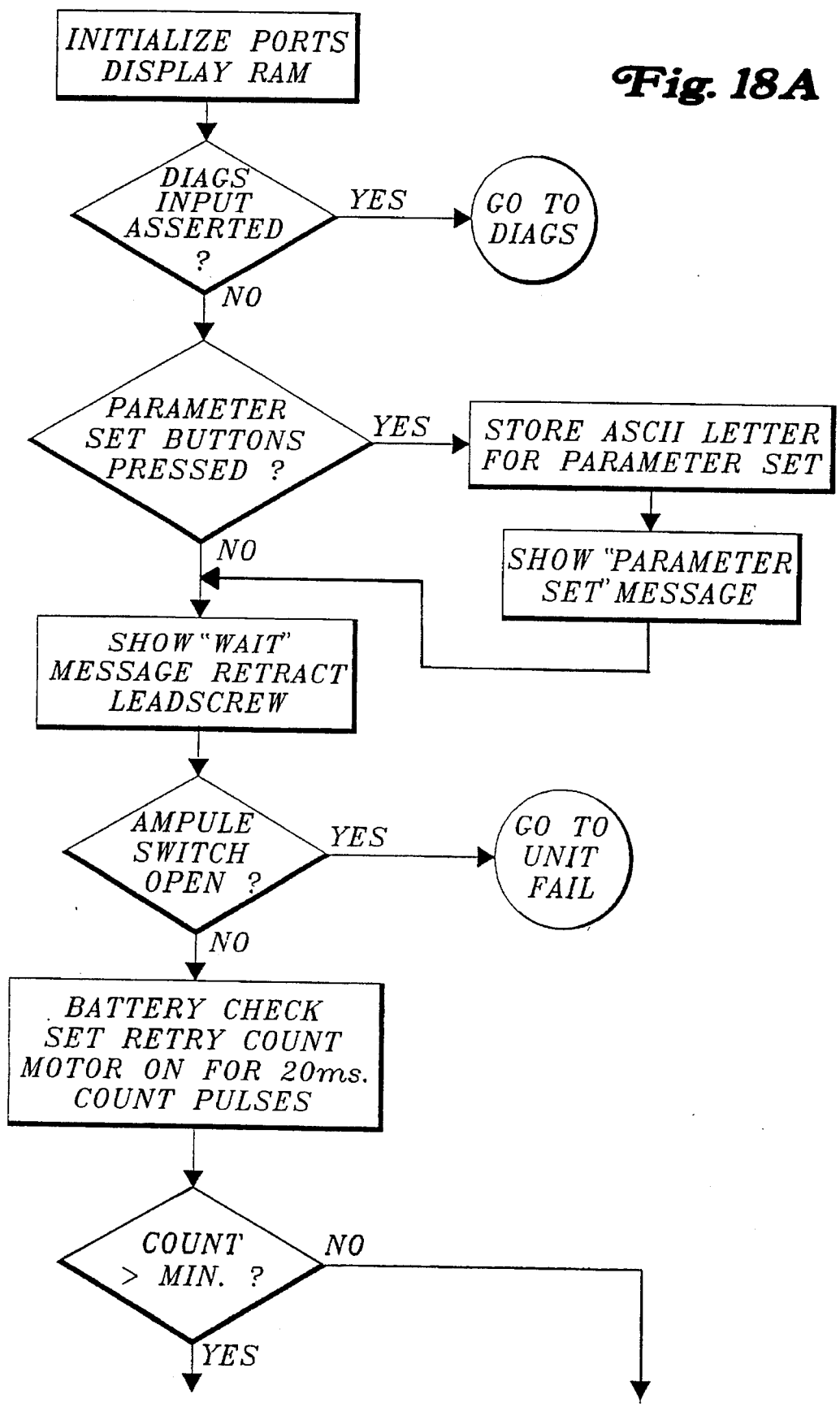
Figure 18B:
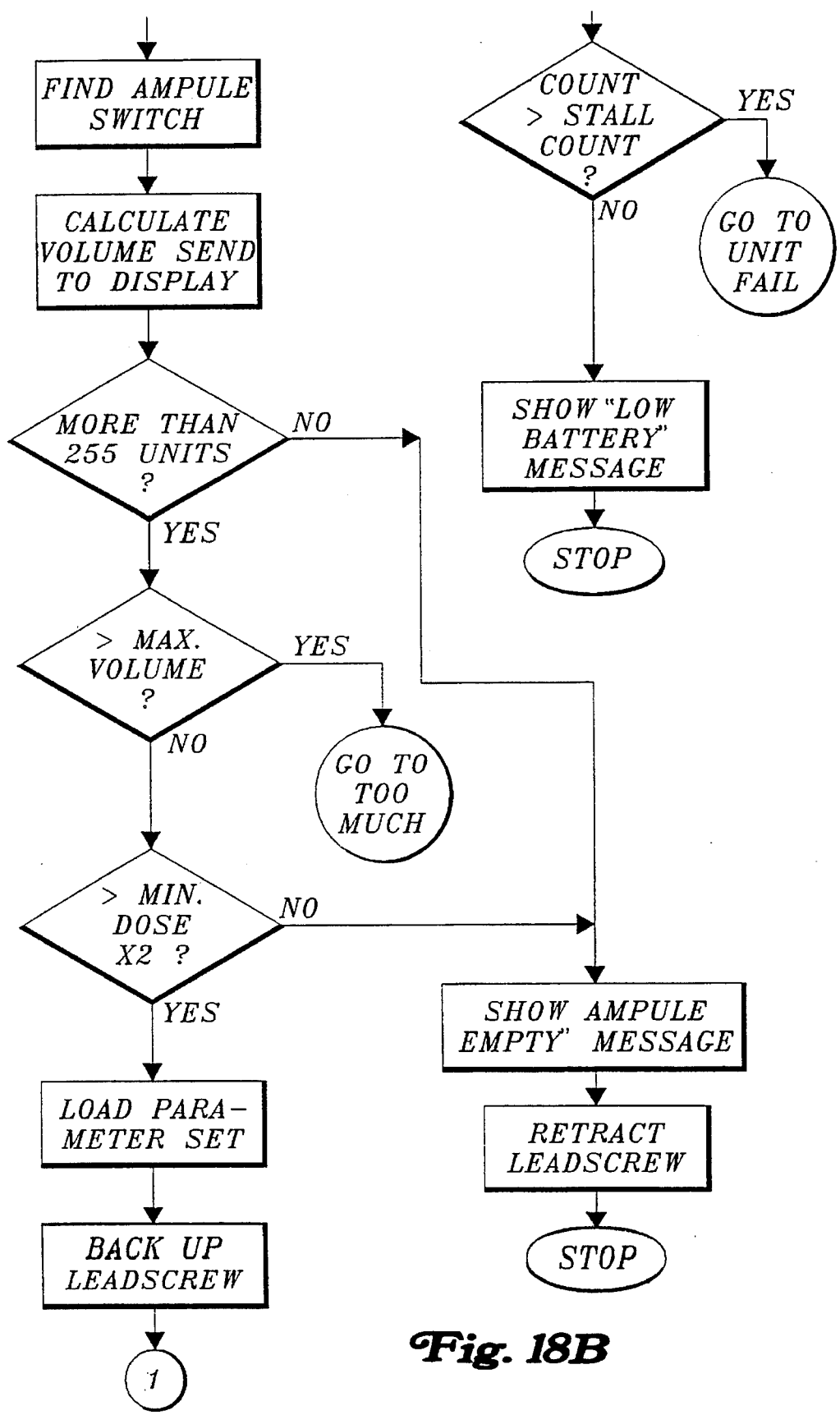
Figure 19:
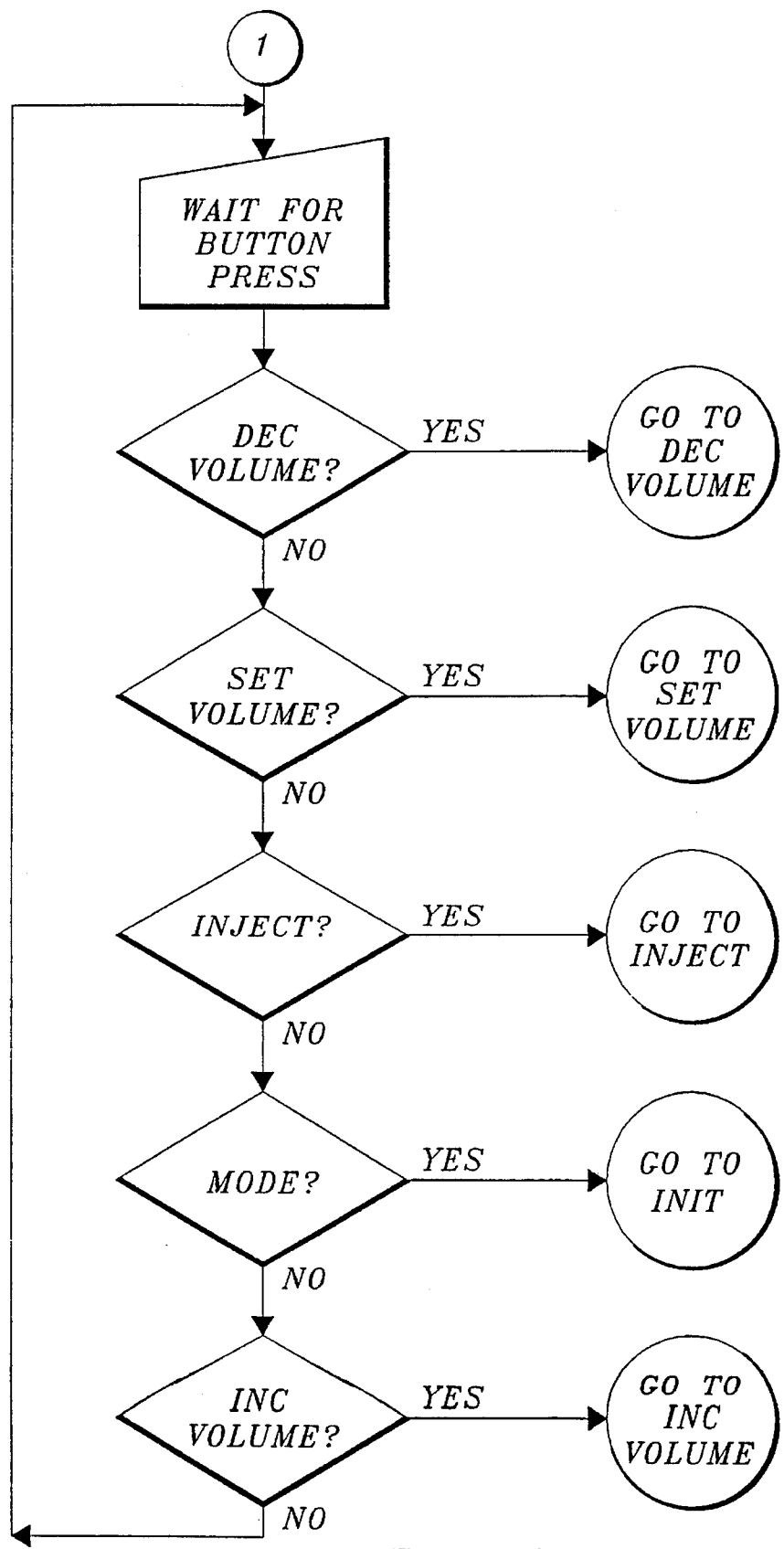
Figure 20:
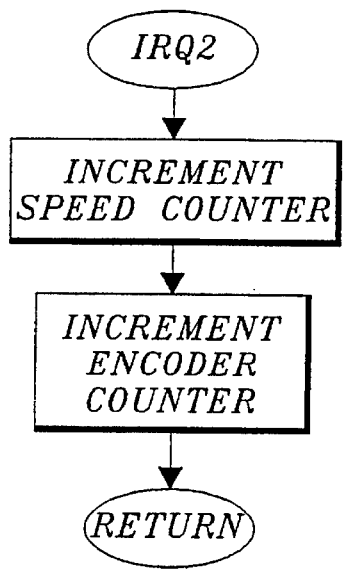
Figure 21:
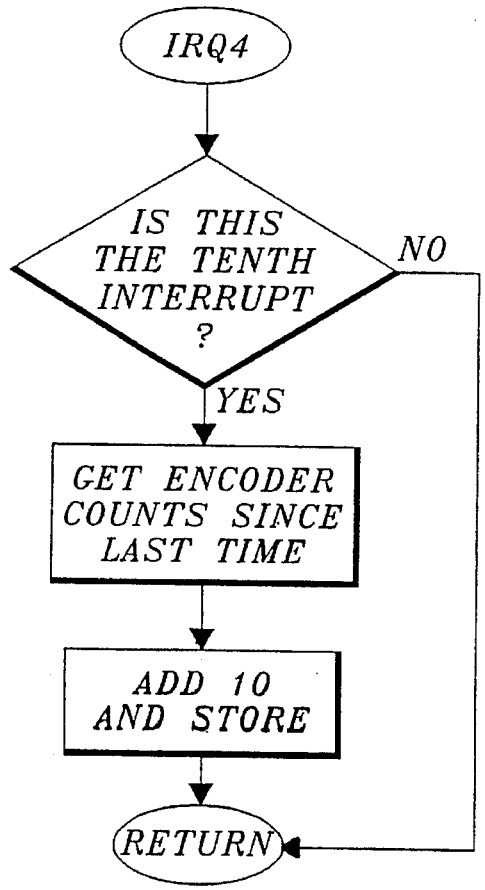
Figure 22:
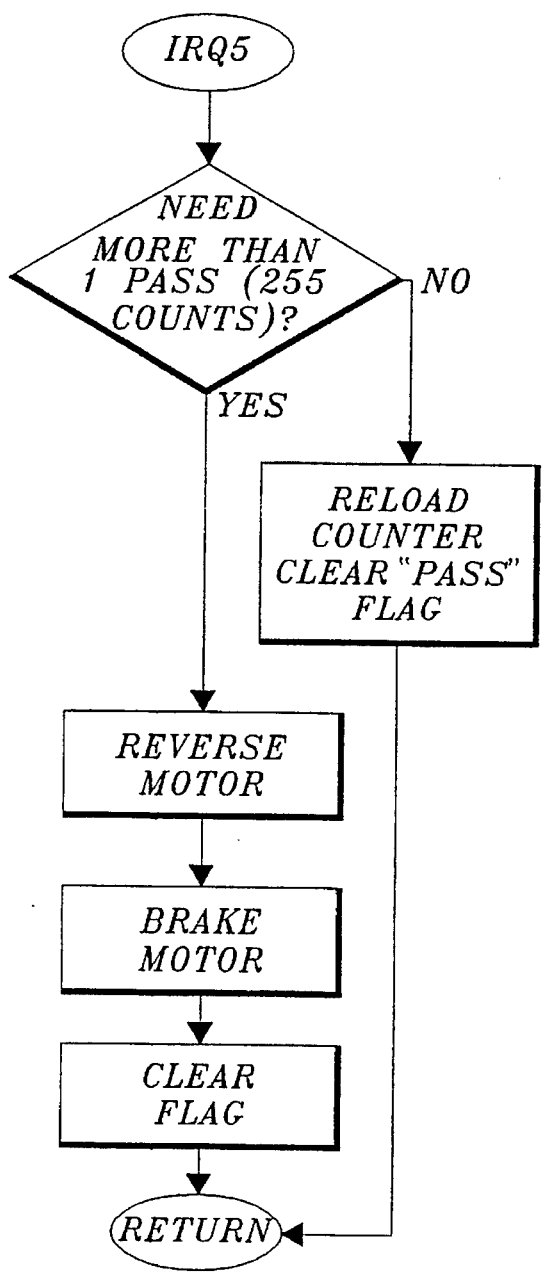
Figure 23:
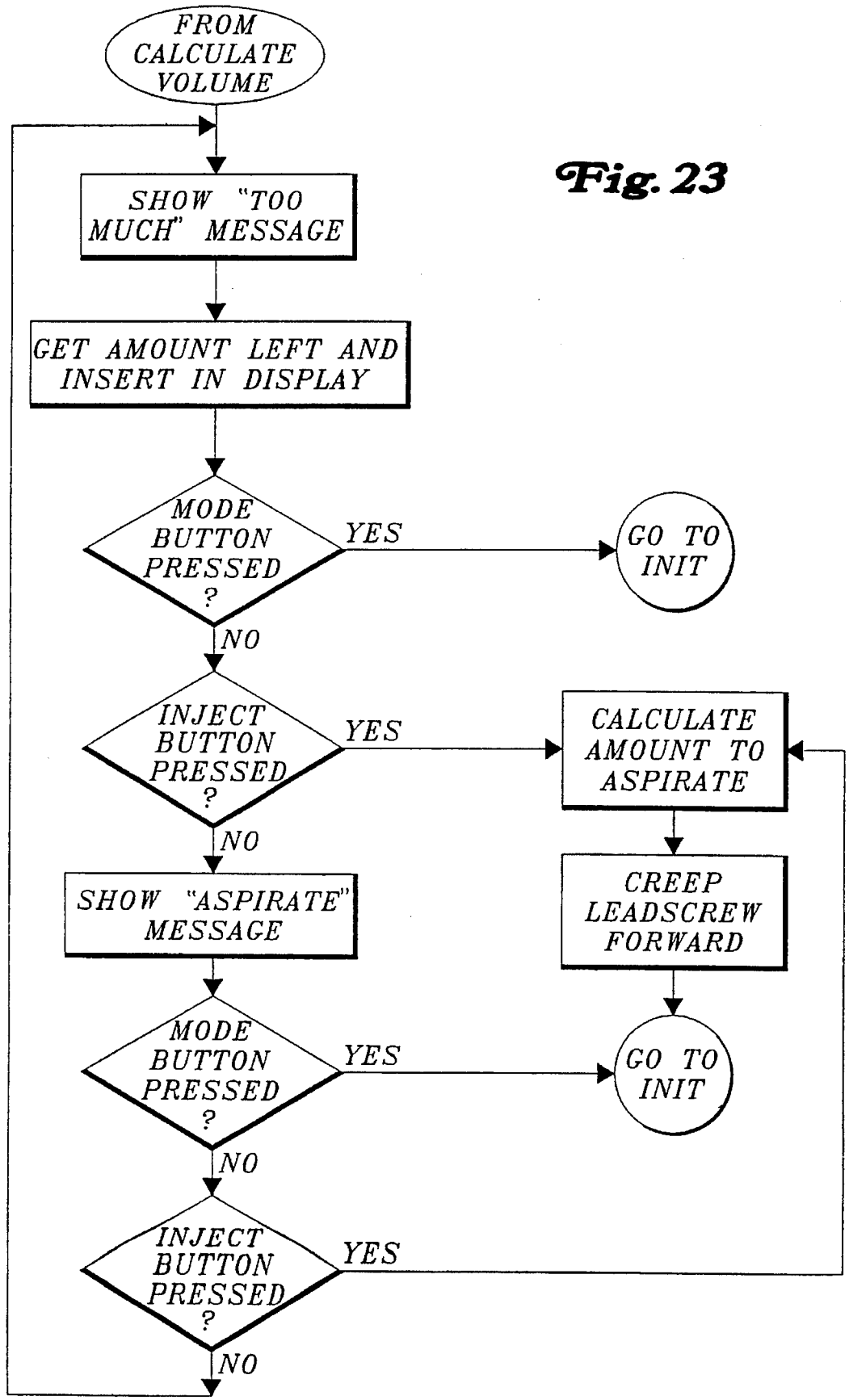
Figure 24:
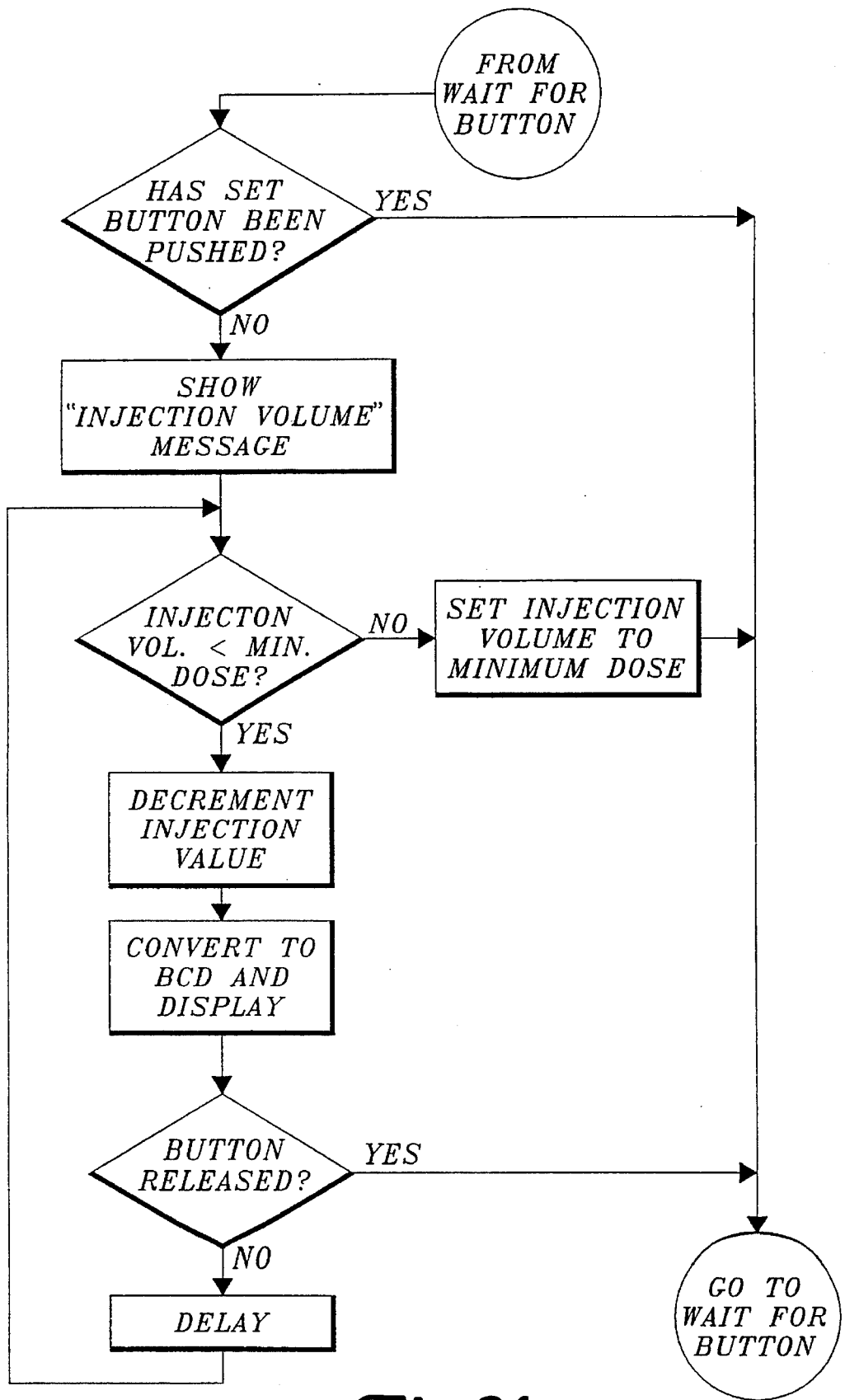
Figure 25:
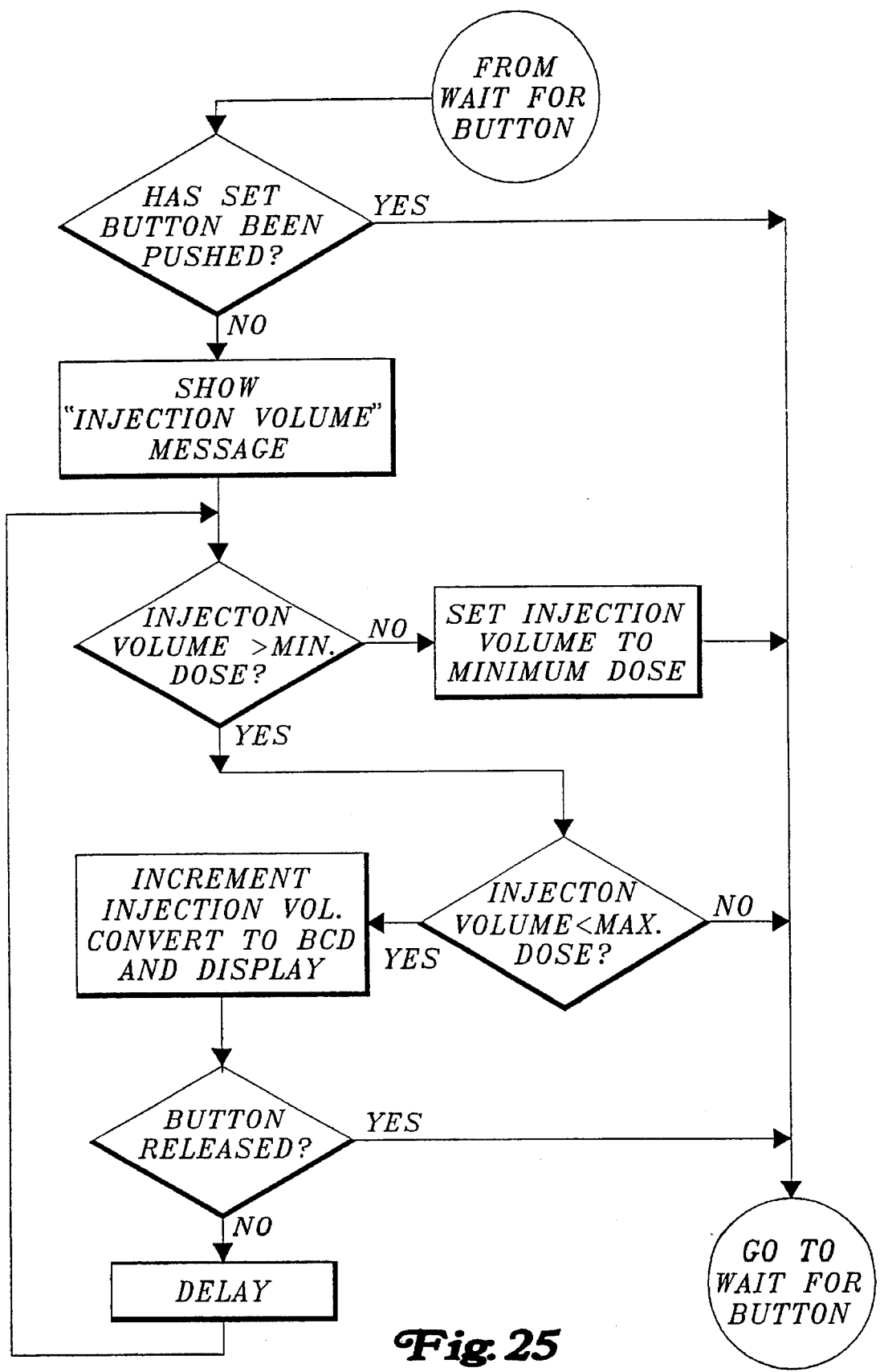
Figure 26:
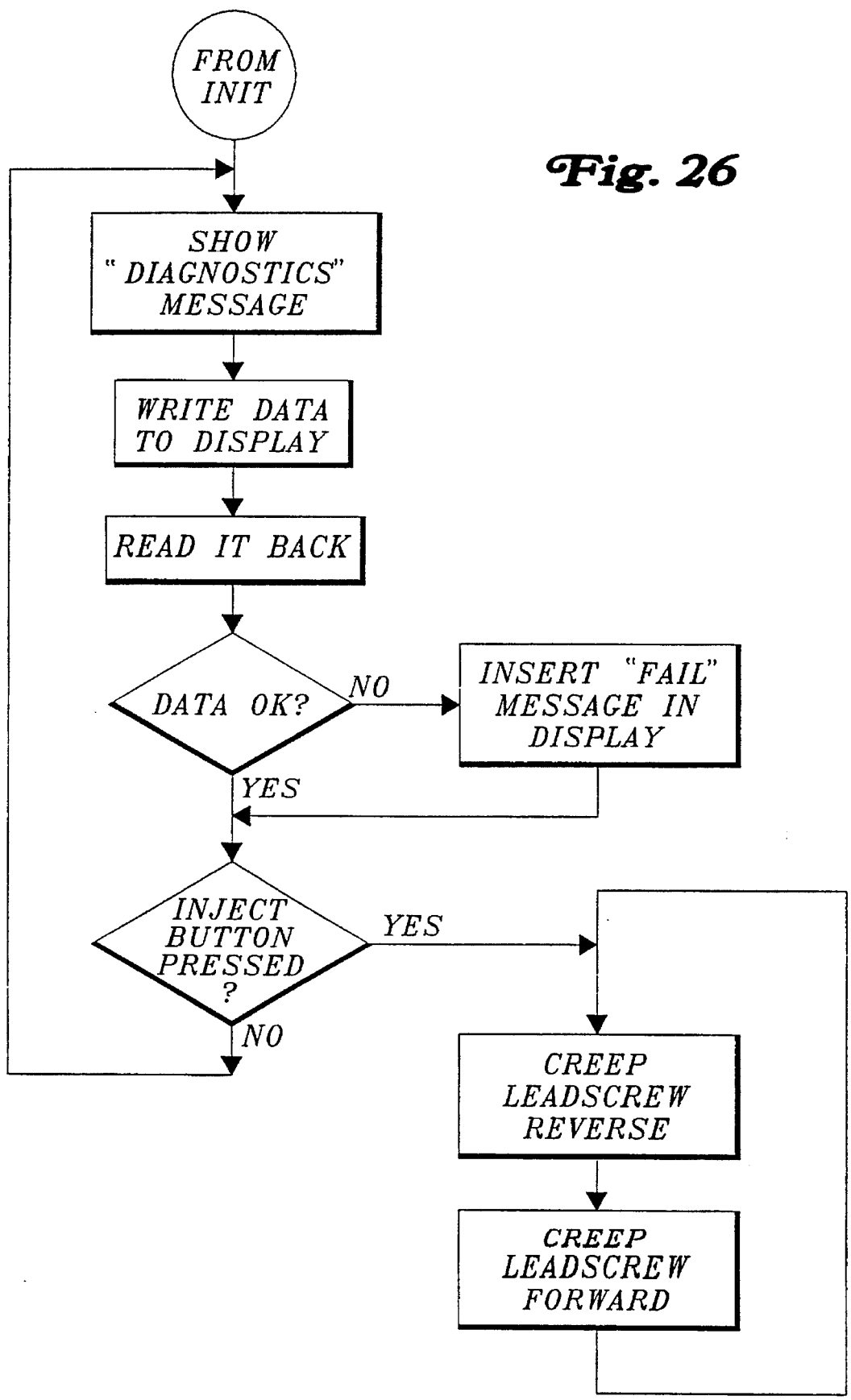
Figure 27:
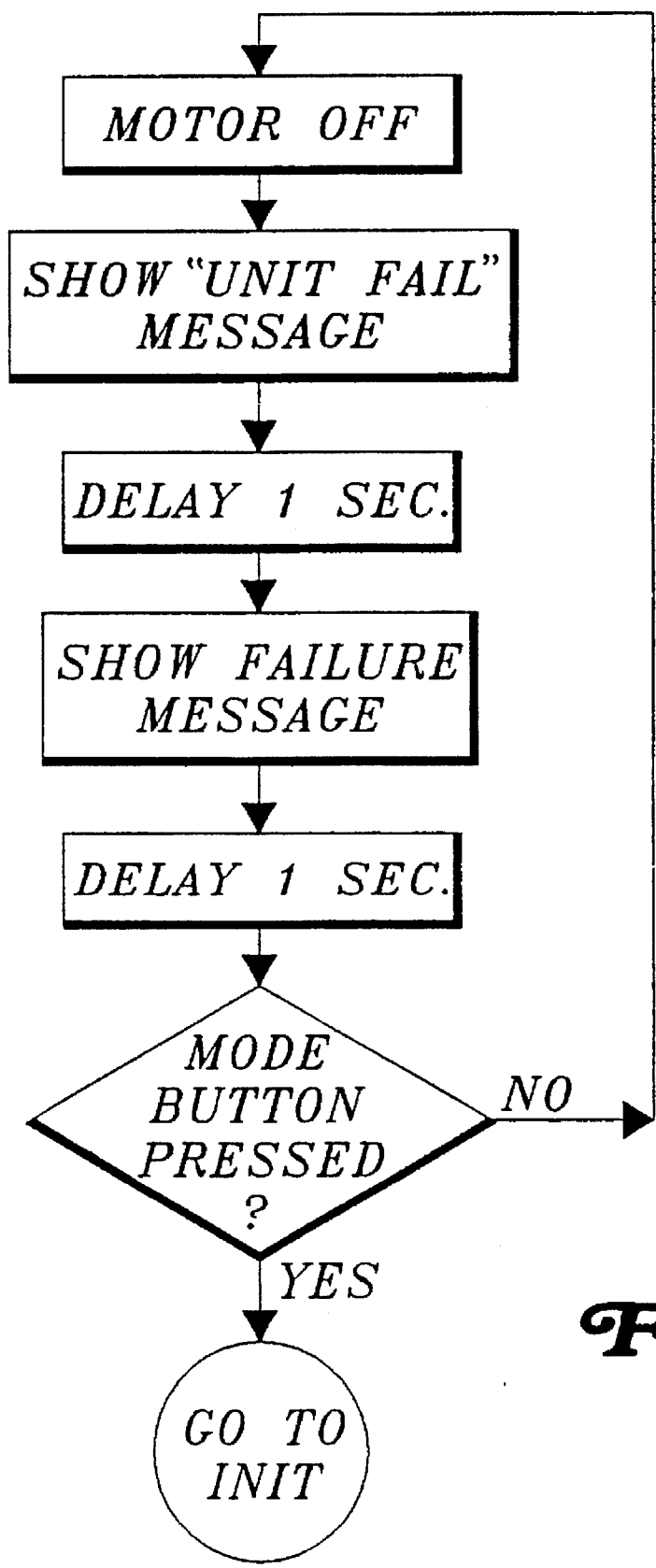
Figure 28:
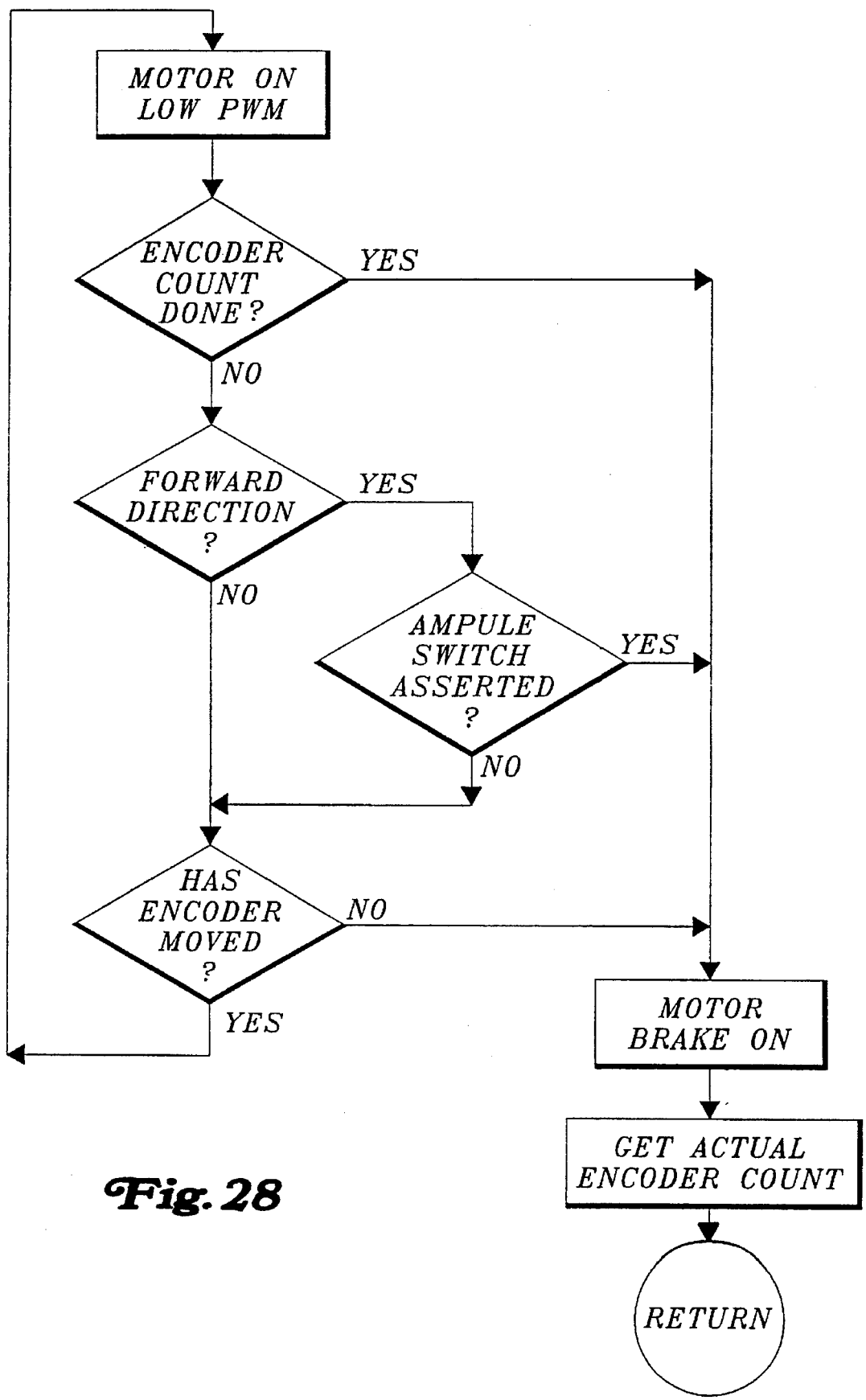
Figure 29:
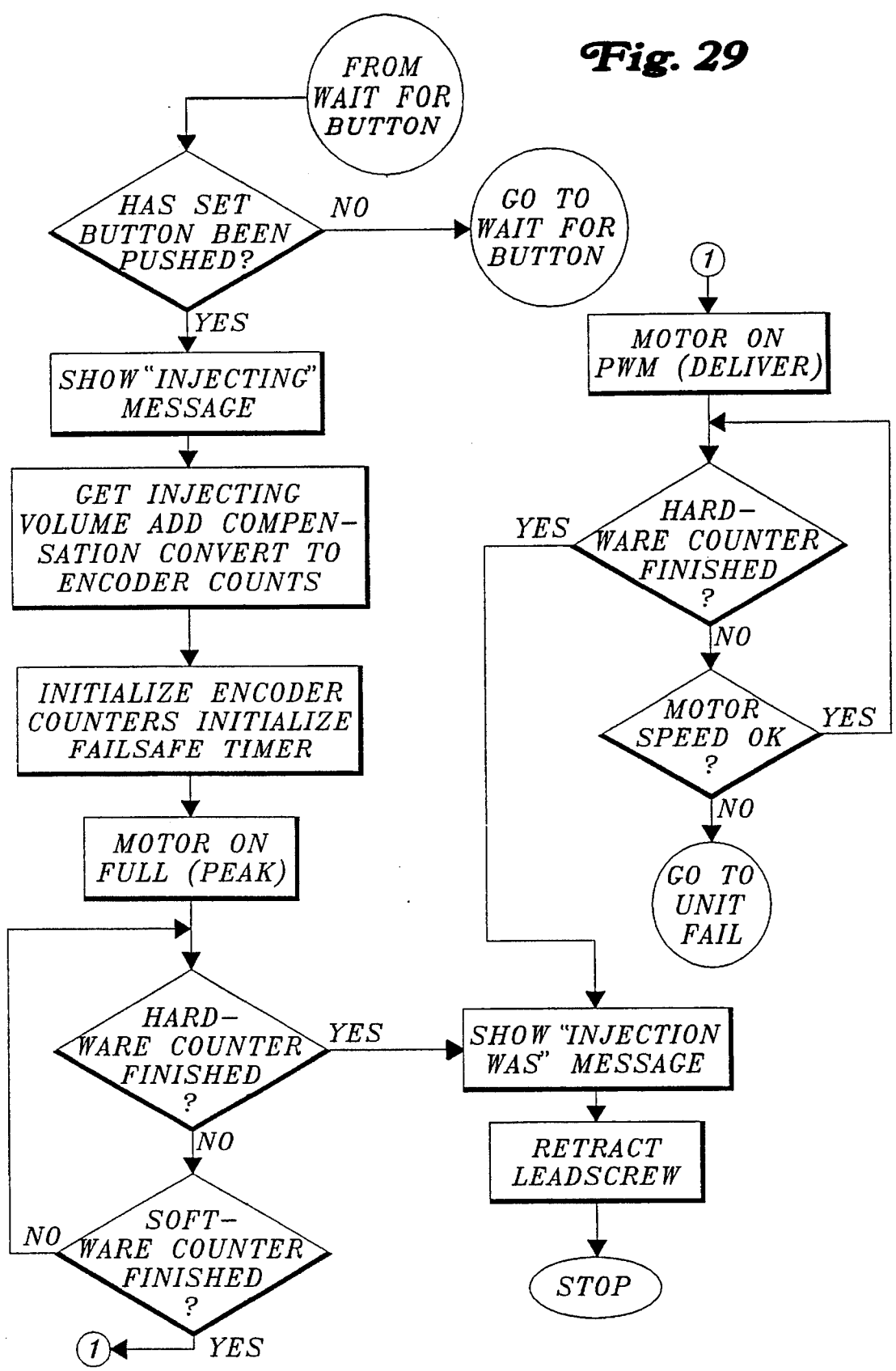
Figure 30:
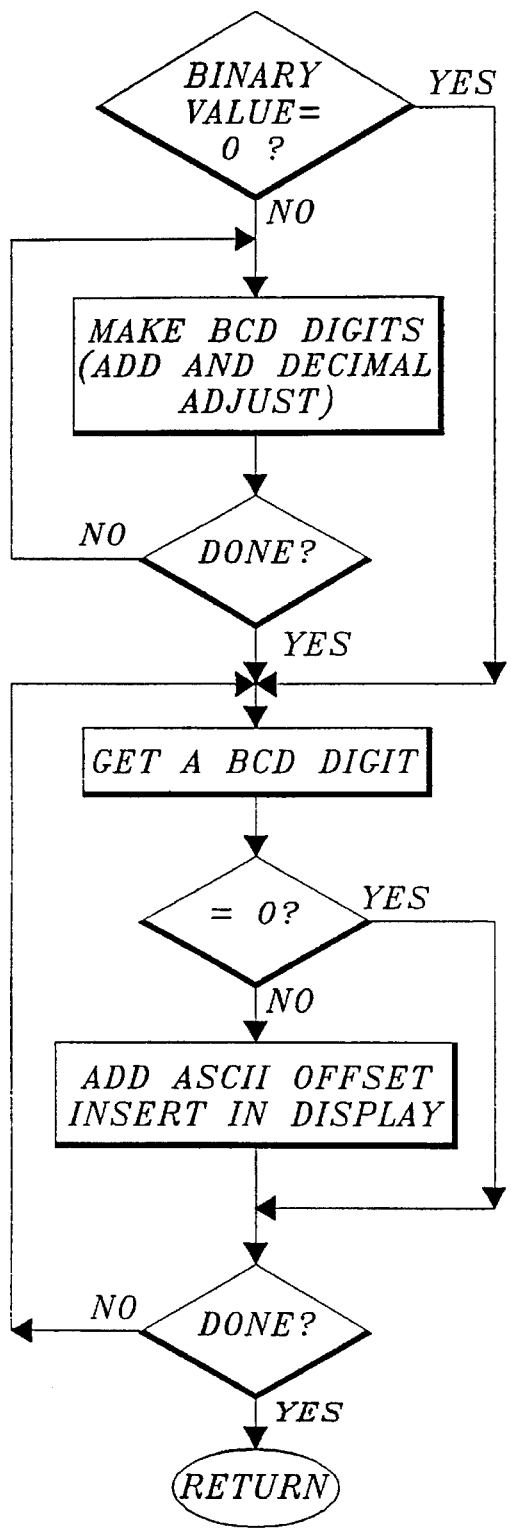
Figure 31:
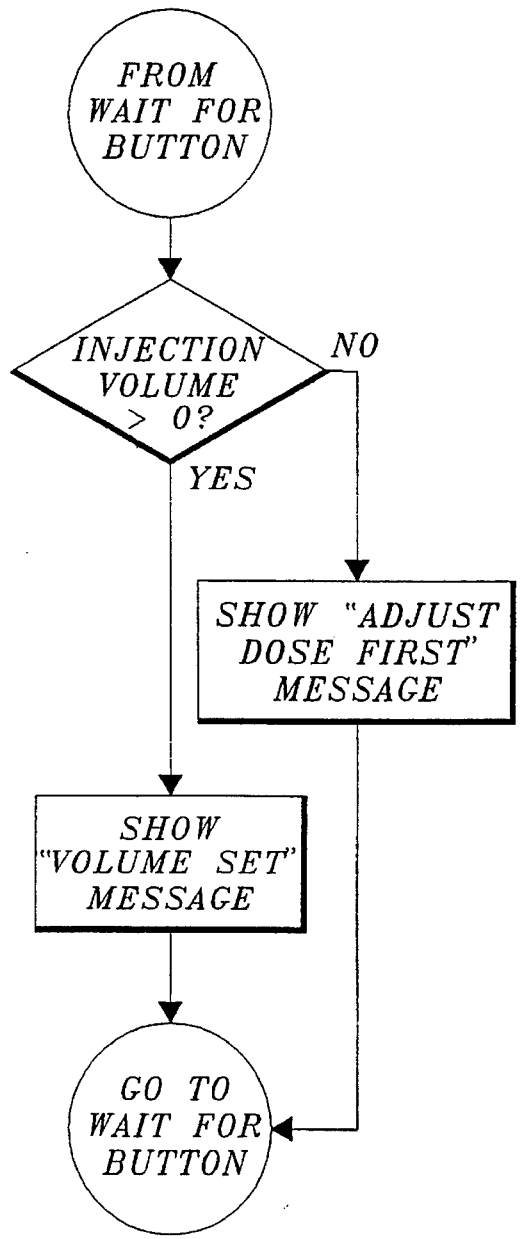

With this type of jet injection, the necessary pharmacokinetics of insulin delivered with a needle/syringe, can be achieved with jet injection. The CPU controls delivery of the jet of fluid to the subcutaneous tissue. Clinical trials show this control achieves insulin time action profiles comparable to a needle/syringe. FIG. 16 shows the results of use of the injector 20 in tests conducted at the Portland Diabetes Clinic, Portland, Oreg., in 1993. The trace A shows Insulin absorption using a needle/syringe, while the trace B shows Insulin absorption using the present injector 20. While trace B shows somewhat higher absorption, during the first 5–6 hours after injection, the differences are nominal enough to readily permit use of jet injection of Insulin.

The present injector and method reduce the pain of the needle/syringe delivery process, as well as the long term tissue scarring effects coming from needle use in chronic diabetics. In addition, the preparation required by the patient in filling and manipulating a needle/syringe required for each self-administered injection is reduced, as the present injector can provide multiple shots over a few days, without additional filling or manipulation. The danger of accidental needle sticks and problems of needle disposal are also reduced.

Thus, while embodiments of the invention have been shown and described, it will be obvious that many changes and modifications may be made without departing from the spirit and scope of the invention.

We claim:

1. A jet injector for providing a jet injection by driving a plunger into an ampule, comprising:

a housing;

an electric motor supported by the housing;

a ball screw driven longitudinally within the housing by the motor;

a controller electrically connected to the motor for controlling the motor speed and direction;

an encoder electrically connected to the controller and positioned to measure rotation of the ball screw, the encoder comprising an encoder wheel rotating in proportion to rotation of the motor;

a detector electrically linked to the controller and positioned to detect when the ball screw contacts the plunger; and means for attaching the ampule to the housing.

2. The jet injector of claim 1 further comprising a control panel on the housing.

3. The injector of claim 1 wherein the motor is coaxial with the ball screw.

4. The jet injector of claim 1 further comprising an electrical energy source within the housing for powering the electric motor and controller.

5. The jet injector of claim 1 wherein the detector is a switch actuated by contact of the ball screw against the plunger.

6. The jet injector of claim 1 further comprising a display on the housing.

7. A jet injector for providing a jet injection by driving a plunger into an ampule, comprising:

a housing;

an electric motor supported by the housing;

a ball screw driven longitudinally within the housing by the motor;

a controller electrically connected to the motor for controlling the motor speed and direction;

an encoder electrically connected to the controller and positioned to measure rotation of the ball screw;

a switch electrically linked to the controller and positioned to actuate when the ball screw contacts the plunger; and means for attaching the ampule to the housing.

8. The jet injector of claim 7 further comprising a display on the housing.

9. The injector of claim 7 wherein the means for attaching comprises a sleeve threaded onto the housing.

10. The injector of claim 7 wherein the motor is coaxial within the ball screw.

11. The jet injector of claim 7 further comprising a control panel on the housing.

12. The jet injector of claim 7 wherein the motor is a DC brushless hollow core motor.

13. The jet injector of claim 7 further comprising an electrical energy source within the housing for powering the electric motor and controller.

14. The injector of claim 7 wherein the encoder comprises an encoder wheel rotating in proportion to rotation of the motor.

15. A jet injector for providing a jet injection by driving a plunger into an ampule, comprising;

a housing;

an electric motor supported by the housing;

a ball screw coaxial with the motor and driven longitudinally within the housing by the motor;

a controller electrically connected to the motor for controlling the motor speed and direction;

an encoder electrically connected to the controller and positioned to measure rotation of the ball screw;

a detector electrically linked to the controller and positioned to detect when the ball screw contacts the plunger; and means for attaching the ampule to the housing.

16. The injector of claim 15 wherein the means for attaching comprises a sleeve threaded onto the housing.

17. The jet injector of claim 15 further comprising a control panel on the housing.

18. The jet injector of claim 15 wherein the motor is a DC brushless hollow core motor.

19. The jet injector of claim 15 further comprising an electrical energy source within the housing for powering the electric motor and controller.

20. The injector of claim 15 wherein the encoder comprises an encoder wheel rotating in proportion to rotation of the motor.

21. The injector of claim 15 wherein the detector is a switch actuated by contact of the ball screw against the plunger.

22. The injector of claim 15 wherein the motor is coaxial with the ball screw.

* * * * *